US012800595B2

(12) United States Patent
Glezer et al.

(10) Patent No.: US 12,800,595 B2
(45) Date of Patent: Nov. 17, 2026

(54) HIGH THROUGHPUT SYSTEM FOR PERFOMING ASSAYS USING ELECTROCHEMILUMINESCENCE INCLUDING A CONSUMABLE SHAKING APPARATUS

(71) Applicant: MESO SCALE TECHNOLOGIES, LLC., Rockville, MD (US)

(72) Inventors: Eli N. Glezer, Del Mar, CA (US); Carl Edens, Highland, MD (US); Bandele Jeffrey-Coker, Damestown, MD (US); Sandor Kovacs, Middletown, DE (US); Christopher Frye, Arlington, VA (US)

(73) Assignee: MESO SCALE TECHNOLOGIES,LLC., Rockville, MD (US)

( * ) Notice: Subject to any disclaimer, the term of this patent is extended or adjusted under 35 U.S.C. 154(b) by 0 days.

(21) Appl. No.: 18/894,461

(22) Filed: Sep. 24, 2024

(65) Prior Publication Data

US 2025/0012822 A1 Jan. 9, 2025

Related U.S. Application Data

(60) Division of application No. 16/938,284, filed on Jul. 24, 2020, now Pat. No. 12,130,297, which is a
(Continued)

(51) Int. Cl.
*G01N 35/00* (2006.01)
*B01F 11/00* (2006.01)
(Continued)

(52) U.S. Cl.
CPC ....... *G01N 35/00029* (2013.01); *B01F 31/22* (2022.01); *B06B 1/16* (2013.01);
(Continued)

(58) Field of Classification Search
None
See application file for complete search history.

(56) References Cited

U.S. PATENT DOCUMENTS 3,430,926 A 3/1969 Freedman et al.
4,047,704 A 9/1977 Hawrylenko
(Continued)

FOREIGN PATENT DOCUMENTS

CN 1053682 A 8/1991
CN 101747397 A 6/2010
(Continued)

OTHER PUBLICATIONS

Office Action issued Nov. 18, 2020 in European Appl. No. 16 777 211.0.
(Continued)

*Primary Examiner* — Brian R Gordon
(74) *Attorney, Agent, or Firm* — MEDLER FERRO WOODHOUSE & MILLS PLLC

(57) ABSTRACT

The present invention relates to a system for performing assays on a solid phase to measure the level of analyte in a sample. Such a system may perform immunoassays using electrochemiluminescence (ECL) including a counterbalanced orbital shaking apparatus for assay consumables.

6 Claims, 23 Drawing Sheets

Related U.S. Application Data continuation of application No. 15/564,581, filed as application No. PCT/US2016/026242 on Apr. 6, 2016, now Pat. No. 10,725,059.

(60) Provisional application No. 62/311,752, filed on Mar. 22, 2016, provisional application No. 62/143,557, filed on Apr. 6, 2015.

(51) Int. Cl.

| | |
|---|---|
| ***B01F 31/22*** | (2022.01) |
| ***B06B 1/16*** | (2006.01) |
| ***G01N 33/543*** | (2006.01) |
| ***G01N 35/10*** | (2006.01) |
| *B01F 101/23* | (2022.01) |

(52) U.S. Cl.

CPC ....... *B06B 1/167* (2013.01); *G01N 33/54366* (2013.01); *G01N 35/00732* (2013.01); *G01N 35/0099* (2013.01); *G01N 35/10* (2013.01); *B01F 2101/23* (2022.01); *G01N 2035/00148* (2013.01)

(56) References Cited

U.S. PATENT DOCUMENTS

| | | | | |
|---|---|---|---|---|
| 4,673,297 | A | 6/1987 | Siczek et al. | |
| 5,122,342 | A | 6/1992 | McCulloch et al. | |
| 5,149,654 | A | 9/1992 | Gross et al. | |
| 5,346,303 | A | 9/1994 | Heinonen et al. | |
| 5,372,425 | A | 12/1994 | Tannenbaum et al. | |
| 5,558,437 | A | 9/1996 | Rode | |
| 5,578,494 | A | 11/1996 | Clark et al. | |
| 6,579,002 | B1 | 6/2003 | Bartick et al. | |
| 8,393,781 | B2 * | 3/2013 | Manera | B01F 35/20 366/112 |
| 8,790,578 | B2 | 7/2014 | Wohlstadter et al. | |
| 9,329,194 | B2 | 5/2016 | Fritchie et al. | |
| 10,203,286 | B2 | 2/2019 | Clinton et al. | |
| 2003/0077583 | A1 | 4/2003 | Ferrara et al. | |
| 2003/0108858 | A1 | 6/2003 | Shah et al. | |
| 2004/0185436 | A1 | 9/2004 | Shah et al. | |
| 2005/0013735 | A1 | 1/2005 | Gebrian et al. | |
| 2005/0074363 | A1 | 4/2005 | Dunfee | |
| 2005/0249634 | A1 | 11/2005 | Devlin, Sr. | |
| 2006/0035368 | A1 | 2/2006 | Malinge | |
| 2006/0160086 | A1 | 7/2006 | Volland et al. | |
| 2007/0177457 | A1 | 8/2007 | Hafner | |
| 2008/0056059 | A1 * | 3/2008 | Manera | B01F 35/2214 366/110 |
| 2008/0057523 | A1 | 3/2008 | Sy et al. | |
| 2008/0299652 | A1 | 12/2008 | Owen et al. | |
| 2009/0117620 | A1 | 5/2009 | Fritchie et al. | |
| 2009/0263904 | A1 | 10/2009 | Clinton et al. | |
| 2010/0203573 | A1 | 8/2010 | Heinonen et al. | |
| 2011/0011740 | A1 | 1/2011 | Roach et al. | |
| 2011/0085409 | A1 | 4/2011 | Malin | |
| 2011/0143947 | A1 | 6/2011 | Chamberlin et al. | |
| 2011/0212041 | A1 | 9/2011 | Tohi et al. | |
| 2011/0269239 | A1 | 11/2011 | Diessel et al. | |
| 2012/0190591 | A1 | 7/2012 | Wohlstadter et al. | |
| 2013/0203620 | A1 | 8/2013 | Glezer et al. | |
| 2013/0323741 | A1 | 12/2013 | Bernet et al. | |
| 2014/0155326 | A1 | 6/2014 | Mark et al. | |
| 2014/0271658 | A1 | 9/2014 | Murphy et al. | |
| 2014/0273191 | A1 | 9/2014 | Tipgunlakant et al. | |
| 2015/0299639 | A1 | 10/2015 | Kleefstra et al. | |
| 2015/0301057 | A1 | 10/2015 | Baron et al. | |
| 2016/0144364 | A1 | 5/2016 | Edwards | |
| 2017/0037146 | A1 | 2/2017 | Zhou et al. | |
| 2018/0010990 | A1 | 1/2018 | Cherubini et al. | |
| 2018/0088141 | A1 | 3/2018 | Vacic et al. | |
| 2018/0147281 | A1 | 5/2018 | Tanaka et al. | |
| 2019/0066846 | A1 | 2/2019 | Nakatsura et al. | |
| 2019/0391170 | A1 | 12/2019 | Kochar et al. | |
| 2020/0105409 | A1 * | 4/2020 | Kochar | G16H 40/67 |
| 2020/0339604 | A1 | 10/2020 | Zak et al. | |
| 2021/0223272 | A1 | 7/2021 | Edens | |
| 2021/0356482 | A1 | 11/2021 | Moffitt et al. | |

FOREIGN PATENT DOCUMENTS

| | | | |
|---|---|---|---|
| CN | 101932932 | A | 12/2010 |
| CN | 202356066 | A | 8/2012 |
| CN | 102753977 | A | 10/2012 |
| CN | 103079704 | A | 5/2013 |
| CN | 103282782 | A | 9/2013 |
| CN | 103988064 | A | 8/2014 |
| DE | 60300580 | T2 | 1/2006 |
| EP | 2301679 | A2 | 3/2011 |
| EP | 2420824 | A2 | 2/2012 |
| GB | 1604884 | A | 12/1981 |
| JP | H04009640 | U | 1/1992 |
| JP | 2002078477 | A | 3/2002 |
| JP | 2002538477 | A | 11/2002 |
| JP | 2003240787 | A | 8/2003 |
| JP | 2004166555 | A | 6/2004 |
| JP | 2004-239778 | A | 8/2004 |
| JP | 2006258692 | A | 9/2006 |
| JP | 2006282332 | A | 10/2006 |
| JP | 2011-518323 | A | 6/2011 |
| KR | 10-2011-0134426 | | 12/2011 |
| WO | 2007/013960 | A1 | 2/2007 |
| WO | 2010/099486 | A1 | 9/2010 |
| WO | 2013/036941 | A2 | 3/2013 |
| WO | 2013110734 | A1 | 8/2013 |
| WO | 2014175018 | A1 | 10/2014 |

OTHER PUBLICATIONS

Office Action issued Nov. 23, 2020 in Indian Appl. No. 201747035255.
Decision to Grant a Patent issued Oct. 6, 2020 in Japanese Patent Appln. No. 2017-552457 (with English language translation). Not In English.
Search Report issued Apr. 29, 2020 in Chinese Patent Application No. 201680033113.9 (in English translation).
Machine Translation of JP 2004166555 to Sanyo Electric Co.
Machine Translation of JP 20020784 77 to Sanyo Electric Co.
Machine Translation of JP 2006282332 to Sanyo Electric Co.
Extended European Search Report issued in connection with the corresponding European Patent Application No. 16 77 7211 on Oct. 25, 2018.
Machine translation of EP 2301679 to Hawrylenko.
International Search Report and Written Opinion issued in connection with the corresponding International Application No. PCT/US2016/026242 on Aug. 19, 2016.
Statement can be found in U.S. Appl. No. 15/564,581, to which this application claims priority.

* cited by examiner

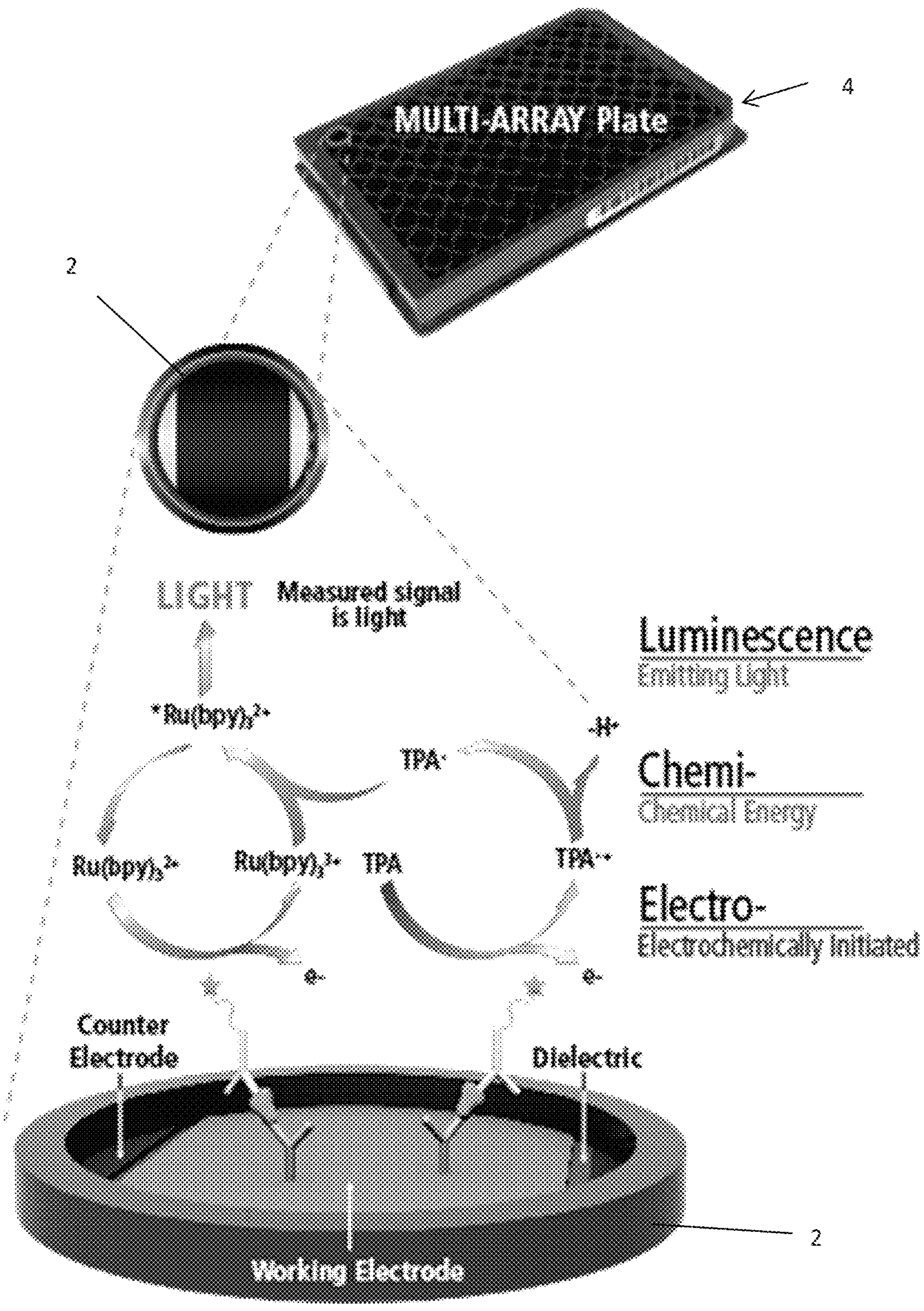
FIGURE 1
(Conventional)

Fig. 11(e)
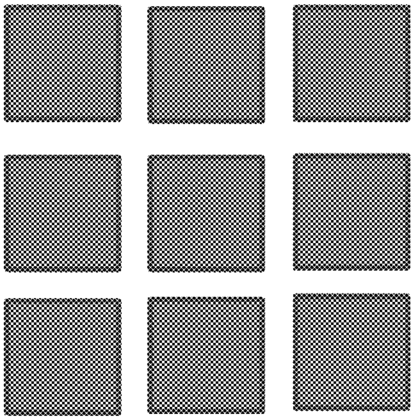
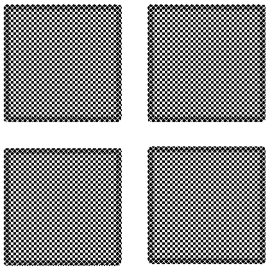
Fig. 11(d)
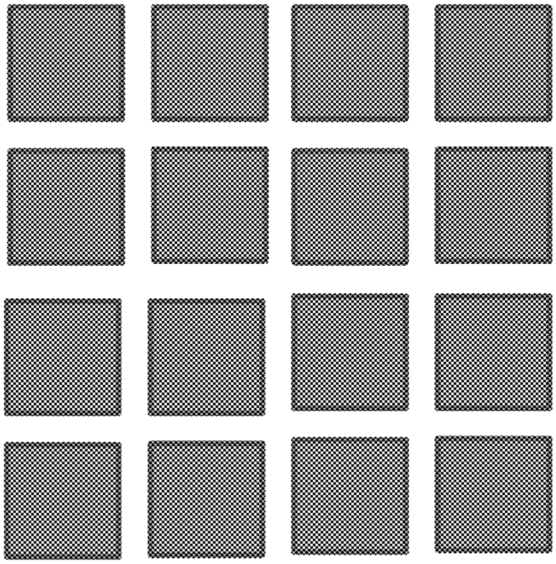
Fig. 11(f)

HIGH THROUGHPUT SYSTEM FOR PERFOMING ASSAYS USING ELECTROCHEMILUMINESCENCE INCLUDING A CONSUMABLE SHAKING APPARATUS

CROSS-REFERENCE TO RELATED APPLICATION

The present application is a divisional of U.S. application Ser. No. 16/938,284, filed Jul. 24, 2020, now U.S. Pat. No. 12,130,297, which is a continuation of U.S. application Ser. No. 15/564,581, filed Oct. 5, 2017, now U.S. Pat. No. 10,725,059, which is a National Stage Entry of International Application No. PCT/US2016/026242, filed Apr. 6, 2016, which claims priority to a provisional application entitled "Consumable Shaking Apparatus" filed on Apr. 6, 2015 bearing Ser. No. 62/143,557, and to another provisional patent application entitled "Throughput System for Performing Assays Using Electrochemiluminescence Including a Consumable Shaking Apparatus" filed on Mar. 22, 2016 bearing Ser. No. 62/311,752, which are incorporated herein by reference in their entireties.

FIELD OF THE INVENTION

The present invention is directed to a system for performing immunoassays using electrochemiluminescence (ECL).

BACKGROUND OF THE INVENTION

The use of binding assays on a solid phase is a common approach to measuring the levels of analytes in a sample. There are many types of natural and synthetic binding reagents (for example, antibodies, nucleic acids, aptamers, receptors, ligands, etc.), solid phases (e.g., the surface of a container or well or the surface of a microparticle) and assay formats (direct binding, sandwich, competitive, etc.) that are known in the art of solid phase binding assays. One specific example that illustrates the types of processing steps that are typical for a solid phase binding assay is a sandwich immunoassay which uses two antibodies directed against the target analyte, one of which is immobilized on a solid phase and the other carrying a label that is detectable through some detection technique (e.g., using fluorescence, chemiluminescence, electrochemiluminescence, absorbance, or the measurement of an enzymatic activity). When the solid phase is the surface of a well in a multi-well plate, typical steps in this format may include: (i) adding a sample to a well and incubating to allow analyte in the sample to be captured by the immobilized antibody in the well; (ii) adding the labeled detection antibody to the well and incubating so that the detection antibody binds to captured analyte to form a labeled "sandwich" complex on the solid phase and (iii) measuring the labels that are present in sandwich complexes on the solid phase.

Optionally, the wells may be washed before or after any of the steps to remove any unbound materials prior to addition of new solutions. During the incubation steps, the plates may be shaken to reduce the time and improve the reproducibility of the binding reactions. One exemplary detection technology that may be used to measure labels during the measuring step is electrochemiluminescence (ECL) detection, which employs labels such as derivatives of ruthenium tris-bipyridine that emit light when in proximity to oxidizing or reducing electrodes under appropriate chemical conditions (see, e.g., U.S. Pat. No. 6,808,939 which is incorporated herein by reference in its entirety). Instrumentation and consumables that are designed to carry out binding assays in multi-well format with ECL detection have been described (see, e.g., U.S. Pat. No. 7,842,246 which is incorporated herein by reference in its entirety). The '246 patent describes multi-well consumables having integrated electrodes within the well that are used as solid phase supports for antibodies or arrays of antibodies. The formation of labeled complexes on the electrodes is measured by applying a voltage to the electrodes and measuring the resultant ECL signal. An ECL read buffer, such as a buffer containing tripropylamine or another tertiary amine (see, e.g., U.S. Pat. No. 6,919,173 which is incorporated herein by reference in its entirety) may be added to the well prior to applying the voltage to provide chemical conditions that lead to efficient generation of ECL. A number of alternative protocols for carrying out ECL assays have also been described including protocols with an additional step during which capture antibodies are immobilized from solution (see, e.g., US Published Patent Application No. 20140256588 which is incorporated herein by reference in its entirety) and protocols where the measurement step includes an amplification step prior to the ECL measurement (see, e.g., US Published Patent Application No. 20140272939 which is incorporated herein by reference in its entirety).

In certain situations, ECL electrodes or other solid phases may be treated with a material (a "blocker" or "blocking reagent") that prevents non-specific binding of analytes or assay reagents. This treatment may be carried out as a separate "blocking" step or blocking reagents may be included in the buffers or diluents used during other steps of an assay procedure. Examples of useful blocking reagents include proteins (e.g., serum albumins and immunoglobins), nucleic acids, polyethylene oxides, polypropylene oxides, block copolymers of polyethylene oxide and polypropylene oxide, polyethylene imines and detergents or surfactants (e.g., classes of non-ionic detergents/surfactants known by the trade names of Brij, Triton, Tween, Thesit, Lubrol, Genapol, Pluronic, Tetronic, F108, and Span).

Heretofore, the steps in ECL immunoassays are completed by various individual machines. For example, the washing of the multi-well plates is accomplished by plate washing machines; the pipetting of samples and reagents into multi-well plates is carried out by mechanized pipetting machines having a large number of pipette tips; the stirring of the samples and antibodies is carried out by mechanical shakers; and the excitation of analyte-antibody complexes and sensing of the emitted light are conducted by plate reading machines. However, there remains a need in the art for an overall system that integrates all these individual machines into a single interconnected system that improves efficiency, provides the ability to clean multiple pipette tips during a run, and provides thermal control to satisfy the operating temperature ranges of the reagents and/or the samples.

SUMMARY OF THE INVENTION

One aspect of the present invention is directed to a method of operating an ECL immunoassay system comprising a number of assay trays, wherein each plate is processed completely before a next tray is processed and an incubation period of the plate divided by a processing period for each tray equals the number of trays to be processed.

Another aspect of the present invention is directed to a method for operating an ECL immunoassay system, said system comprising a pipette dispenser, a plurality of multi-well plates adapted to store ECL complexes attached to electrodes contained in the multi-well plates, an incubator and an ECL reader. The inventive method comprises the following steps:

a. removing a single multi-well plate from a shelve,
b. optionally, washing said single multi-well plate,
c. depositing a sample to be tested into the wells on said single multi-well plate,
d. depositing at least one reagent to form complexes with analytes in the sample,
e. optionally, washing said single multi-well tray to remove remaining analytes,
f. placing the washed single multi-well plate in the incubator,
g. repeating steps (a)-(f) with another single multi-well plate until the incubator is full, wherein a period of incubation is the sum of the time to fill the incubator with multi-well plates, h. placing a fully incubated multi-well plate in the ECL reader.

Step (h) is repeated until all incubated plates are placed in the ECL reader. The number of multi-well plates stored in the incubator is equal to the incubation period divided by a time to complete steps (a)-(f).

Another aspect of the present invention relates to an ECL immunoassay system comprising a housing that encloses a pipette dispenser, a plurality of multi-well trays adapted to hold ECL complexes attached to electrodes contained in the tray, an incubator, an ECL reader and a cooler. The cooler is located proximate to a back surface of the housing and the housing further comprises a flow plenum that directs an air flow from the cooler to a front surface of the housing. In one embodiment, the flow plenum is located proximate a top surface of the housing. In another embodiment, the flow plenum is located proximate a bottom surface of the housing.

The top flow plenum is a space between the top surface and a second top surface located below the top surface. The second top surface comprises at least one ingress opening proximate to cooler and at least one egress opening the front surface. The cooler can be one or more thermoelectric coolers.

Another aspect of the present invention is related to a pipette tip washing system comprising at least one chimney defining an opening adapted to receive at least one pipette tip, wherein a gap between the at least one pipette tip and the at least one chimney is substantially constant, wherein said at least one chimney is fluidly connected to a cleaning fluid, wherein said cleaning fluid is pumped through said gap to clean an outside of said at least one pipette. A level sensor may be attached to a side wall of a housing of the apparatus. A flow restrictor can be located between the at least one chimney and a manifold in fluid communication with the cleaning fluid.

Yet another aspect of the present invention is directed to a method for washing pipette tips comprising (a) a plurality of steps of washing an inside of the pipette tips, which includes progressively increasing aspirated volumes of washing liquids of increasingly purer water, and
(b) a plurality of steps of washing an outside of the pipette tips using the same washing liquids, wherein the pipette tips are placed proximate a gap of constant thickness to control the flow of washing liquids.

The method may also comprise a step of washing the pipette tips is a solution of water and bleach prior to steps (a) and (b). This method may also include a physical inactivation of the pipette tips to minimize carryover of the sample to be tested and/or one or more reagent(s).

The present invention also relates to a counterbalanced assay consumable shaking apparatus comprising (a) an orbital shaker assembly comprising a horizontal orbiting platform and (b) an assay consumable storage assembly positioned on the platform. The storage assembly comprises (i) a shelving subassembly comprising a plurality of sets of vertically aligned storage units, wherein each storage unit is sized to accommodate a consumable and comprises a consumable latching mechanism; and (ii) a counterweight positioned within the storage assembly at a height corresponding to the center of mass of the storage assembly and the orbiting platform. The apparatus further comprises a rotating axle extending from the shaker assembly to the storage assembly in a vertical direction and the counterweight is operatively connected to the rotating axle.

The present invention further relates to a counterbalanced assay consumable shaking apparatus comprising (a) an orbital shaker assembly comprising a horizontal orbiting platform; and (b) an assay consumable storage assembly positioned on the platform. The storage assembly comprises (i) a shelving subassembly comprising a plurality of sets of vertically aligned storage units, wherein each storage unit is sized to accommodate a consumable and comprises a consumable latching mechanism, and (ii) two or more counterweights positioned within the storage assembly, wherein one counterweight is positioned above and another counterweight positioned symmetrically below a height corresponding to the center of mass of the storage assembly and the orbiting platform. The apparatus further comprises a rotating axle extending from the shaker assembly to the storage assembly in a vertical direction and each of the two or more counterweights are operatively connected to the rotating axle. Alternatively, the apparatus comprises two or more rotating axles in operative communication with a timing belt and each rotating axle is connected to a counterweight.

Another aspect of the present invention is directed to a method of operating an assay system to analyze a batch of assay plates, wherein (i) each plate in said batch undergoes a series of different processing cycles of time length N,
(ii) for a given plate in said batch, the different processing cycles in said series are separated by incubation periods of at least time Y,
(iii) each of the different processing cycles in said series is carried out sequentially on the plates in said batch, and
(iv) the number of plates in the batch is less than or equal to Y/N.

Another aspect of the present invention is further directed to a method of operating an assay system to analyze a sequence of assay plates, wherein (i) each plate in said batch undergoes a series of different processing cycles of time length N,
(ii) at least one of said cycles in said series is an interleaved cycle divided into pre-incubation subcycle of length A and a post-incubation subcycle of length B, wherein A+B=N and for a given plate, the completion of said subcycle of length A and the commencement of said subcycle of length B is separated by an incubation time that is a multiple of time N,
(iii) carrying out said interleaved cycle on said sequence of plates by
  (a) identifying the first plate in said sequence that has not undergone the pre-incubation subcycle and carrying out said pre-incubation subcycle on it or, if no plates are available for pre-incubation processing then idling for time A and (b) identifying the first plate in the sequence that has completed the incubation, but not undergone the post-incubation subcyle and carrying out said post-incubation subcycle on it or, if no plates are available for post-incubation processing then idling for time B, and (iv) repeating step (iii) until all the plates in the sequence have undergone the pre-incubation and post-incubation subcycles.

The assay system may comprise a plate moving robot, a processing deck, a plate hotel (or shelves), a pipette dispenser, a plate washer, a shaking incubator and a plate reader. The assay plates may comprise electrodes for carrying out ECL measurements and the plate reader is an ECL reader.

The processing cycles comprise one or more of the following steps:

a. using said robot to move a single assay plate of said batch from the hotel or incubator to the deck,
b. using said robot to move a sample or reagent plate from the hotel or incubator to the deck,
c. using the pipettor to transfer samples or reagent from said sample or reagent plate on said deck to said assay plate on said deck,
d. using said plate washer to wash the wells of said assay plate on said deck,
e. using said robot to transfer said assay plate on said deck to said hotel or incubator,
f. using said robot to transfer said assay plate to said plate reader.

The different processing cycles may also comprise at least one of:

(i) a sample addition cycle,
(ii) a detection reagent addition cycle,
(iii) a plate read cycle, and
(iv) a blocking cycle.

The processing cycles may further include the step of incubating an assay, sample or reagent plate and said incubation time is less than time N.

At least one of one processing cycle may be an interleaved cycle divided into pre-incubation subcycle of length A and a post-incubation subcycle of length B, wherein A+B=N and for a given plate, the completion of said subcycle of length A and the commencement of said subcycle of length B is separated by an incubation time that is a multiple of time N. The interleaved cycle can be carried out on said batch of plates by (i) identifying the first plate in said batch that has not undergone the pre-incubation subcycle and carrying out said pre-incubation subcycle on it or, if no plates are available for pre-incubation processing then idling for time A and
(ii) identifying the first plate in the batch that has completed the incubation, but not undergone the post-incubation subcyle and carrying out said post-incubation subcycle on it or, if no plates are available for post-incubation processing then idling for time B, and
(iii) repeating step (ii) until all the plates in the batch have undergone the pre-incubation and post-incubation subcycles.

BRIEF DESCRIPTION OF THE FIGURES

In the accompanying drawings, which form a part of the specification and are to be read in conjunction therewith and in which like reference numerals are used to indicate like parts in the various views:

FIG. 1 is a diagram showing an exemplary redox ECL reaction in an immunoassay;

FIG. 10(*c*) is an expanded view of the top eccentric mount and the counterbalance shown in FIG. 10(*b*); and FIG. 10(*d*) is a top view of the driving mechanism and the bottom eccentric mounts;

DETAILED DESCRIPTION OF VARIOUS EMBODIMENTS

Unless otherwise defined herein, scientific and technical terms used in connection with the present invention shall have the meanings that are commonly understood by those of ordinary skill in the art. The terms "tray" and "plate" are used interchangeably herein. The term "hotel" and "shelve(s)" are also used interchangeably herein. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

Figure 2:
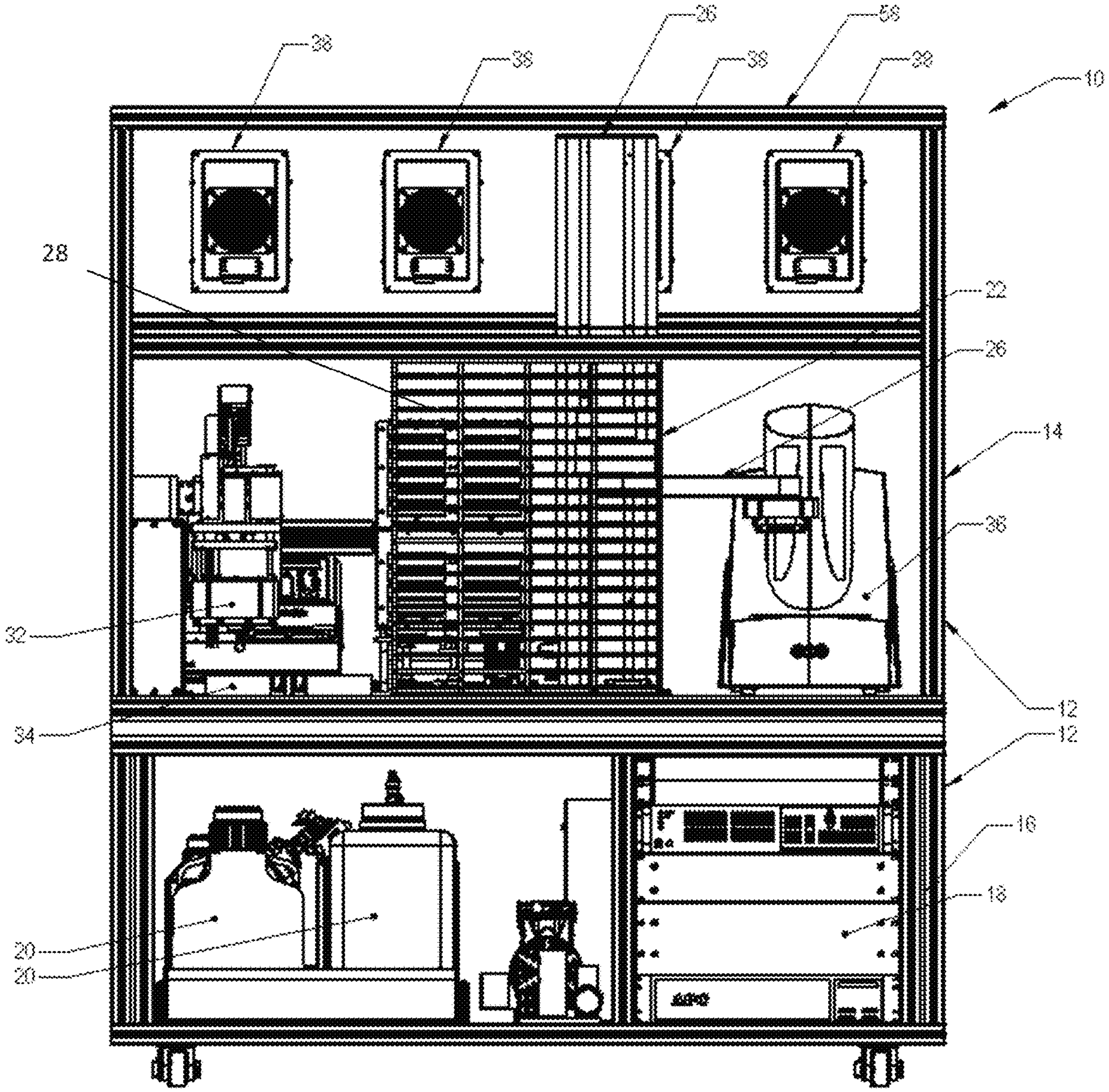
FIG. 2 is a front view of the inventive ECL immunoassay system.
Figure 3:
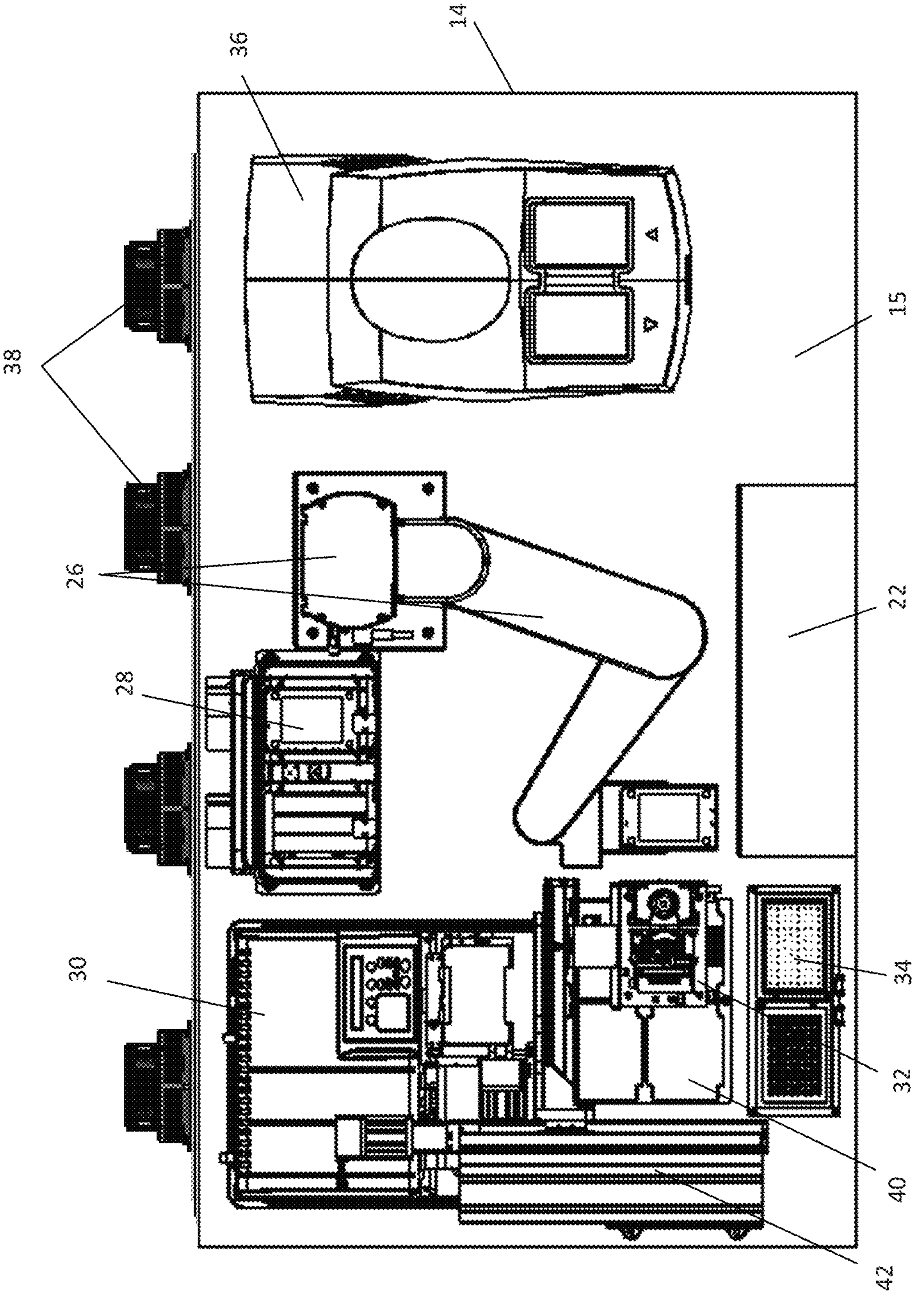
FIG. 3 is a top view of the system of FIG. 2.

One embodiment of the present invention is directed to system 10 as shown in FIGS. 2 and 3. System 10 advantageously handles all the steps of the solid phase binding assays (e.g., ECL immunoassays) described above, and preferably is a fully automated system that can handle a number of multi-well plates 4. The system, as described below, is especially well suited for carrying out ECL-based solid phase binding assays, however, one of average skill in the art could adapt the system to run other assay formats and/or detection technologies using similar processing steps by appropriate selection of the plate reader component and the assay consumables and reagents. All the necessary and optional machineries are contained within housing or enclosure 12, as well as samples, reagents, buffers, washing and cleaning liquids, electronics and waste storages. Preferably, enclosure 12 is supported by castor wheels to render system 10 mobile.

As best shown in FIG. 2, enclosure 12 has upper compartment 14 and lower compartment 16. Upper compartment 14 houses the machineries, samples and reagents. Lower compartment 16 stores electronics 18, which may include a computer, interfaces to control the machineries and to receive data and communication from the machineries, input/output devices including a graphical user interface for technicians and other users to select the proper protocol from a list of predetermined protocols and a WiFi for remote communication with other users. Lower compartment 16 also stores containers 20 to store washing liquids including deionized water with or without surfactants or soaps and store waste or used water, described further below.

Upper compartment 14 houses a number of equipment and machineries mounted on floor or deck 15, including but not limited to shelves 22, also known as hotel 22, sized and dimensioned to store a plurality of trays that contain samples or reagents or that will be used in the assay process, bar code reader 24 (not shown) located below shelves 22, and robot arm 26 designed to deliver the trays and their lids (if available) to other machineries and return them to shelves 22. Upper compartment 14 also contains shaker and incubator 28, plate washer 30 designed to wash unattached materials from the wells of multi-well assay plates, multiple channel pipettor 32 for delivering liquids to the wells of multi-well assay plates and, pipette tip washing manifold 34 to clean the pipette tips from pipettor 32 after each use. Upper compartment 14 also houses tray/plate reader 36 and thermoelectric coolers 38, which are solid state coolers. Plate reader 36 is, preferably, an ECL plate reader for carrying out measurements based on the ECL reaction depicted in FIG. 1. Alternatively, other types of plate readers (such as absorbance, fluorescence or chemiluminescence-based plate readers) could be used to carry out assays using other detection approaches.

Also mounted on deck 15 are pipetting deck 40, which in this embodiment contains four spaces sized and dimensioned to retain four trays, and gantry 42, which supports multichannel pipettor 32 for movement along deck 15 in three-dimensions. Preferably, pipette tip washing manifold 34 comprises two manifolds 34*a* and 34*b*, each contains a number of chimneys corresponding to the number of pipette tips being used. Preferably, one manifold contains water with a small amount of surfactant, such as those discussed above in connection with the blocking reagents, and the other manifold contains deionized water, described further below.

Before assay system 10 is started, the plates that will be used in the assay process are loaded onto shelves 22. Any multi-well plates can be used so long as the plates are sized and dimensioned to work with the machineries. Preferably, the shape and dimensions of the plates are in conformance with established standards for assay plates—such as those set by the Society for Laboratory Automation and Screening (SLAS)—and the plate-processing components (such as the plate washer, pipettor, reader, robot arm, etc.) are configured to process plates meeting the same standards. To enable high-throughput parallel processing of multiple samples, the assay plates 4 used for carrying out assay reactions are preferably multi-well plates. Preferably, the number and arrangement of wells follows an established standard such as the 24-well, 96-well, 384-well and 1536-well formats (most preferably, the 96-well plate format), although any well arrangement is possible. For carrying out ECL-based assays, assay plates as described in U.S. Pat. No. 7,842,246 may be used. The highest throughput can be achieved by using components that simultaneously process all the wells in a plate simultaneously. For example, for processing 96-well assay plates, system 10 preferably comprises a 96-channel pipettor and 96-channel plate washer.

In addition to the assay plates, other plates may be loaded that provide samples to be tested or reagents used in the assays such as assay diluents, detection reagents, read buffer (e.g., TPA solution), blocking agents, and tip washing reagents (e.g., bleach solution). These plates may have a multi-well format, preferably with the same well density as the assay plates. The use of multi-well plates is advantageous when it is desirable to transfer different samples or reagents into the different wells of an assay plate. Reagents or samples that will be transferred to all the wells of a plate can also be provided in multi-well plates, or they can be provided in plates having a single large well (i.e., a reagent reservoir). Advantageously, the wells of the plates used for samples and/or reagents may be conical or round-bottom wells to reduce dead volume. The plates may be sized so that the volume of liquid is sufficient for only one assay plate, or for multiple assay plates (e.g., through the use of higher volume deep well plates. Plates that store the samples and reagents are positioned in predetermined locations on shelves 22. These positions are preselected when defining the protocol so that robot arm 26 knows where to extract and return the plates or reservoirs. Robot arm 26 is controlled by the computer stored in lower compartment 16, which also contains the software to operate system 10.

To start system 10, an operator selects a protocol among a list of protocols to be executed. Protocols are chosen based in part on the assay format to be performed. Illustrative assay formats are described below. Robot arm 26 preferably checks whether the plates and reservoirs are located where they are supposed to be and whether certain plates, such as the plates/reservoirs containing the samples or antibody reagents, have a lid to minimize evaporation. Preferably, all plates and reservoirs have bottom surfaces of substantially the same size, so that all can fit snugly on tray pipette deck 40. The operating computer would notify the operator if a tray or reservoir is mis-located or is missing a lid. Each plate 4 or reservoir placed on shelves 22 preferably has a bar code, as best shown in FIG. 1. Bar code reader 24 can read these bar codes and communicate to the operating computer whether the correct tray or reservoir is loaded on shelves 22. After this check, robot arm 26 would extract one or more trays, e.g., an assay plate 4, a sample plate containing samples to be tested and/or a reagent plate (for example, a plate containing a diluent, blocker or a detection reagents such as antibodies labeled with ECL labels), and place the plates on plate pipetting deck 40. Optionally, the assay plate may be transferred to the plate washer and washed prior to placement on deck 40.

Thereafter, multichannel pipettor 34 may perform a number of preselected actions according to the selected protocol. In one possible protocol, pipettor 34 uses 96 pipette tips to aspirate detection reagents from the wells of the reagent plate and inject a defined volume of the same into the wells of an assay plate with immobilized antibodies on the surface of each well (for example, an ECL assay plate with antibodies immobilized on an electrode in each well). The pipettor then uses a similar process to transfer a defined volume of each sample from the wells of the sample plate to the wells of the assay plate. Robot arm 26 can put the assay plate with the samples and detection reagents into shaker/incubator 28 to mix the samples and detection reagents while incubating same. During the period when the plate is incubating, additional plates may be processed in series using the same set of operations.

After the samples and detection reagents are fully incubated, robot arm 26 removes the tray from shaker/incubator 28 and brings it to the plate washer 30. Plate washer 30 has a pair of tubes for each well. One tube injects a washing liquid from a container 20 stored in lower compartment 16 into the well and the other tube aspirate the same well and discards the used liquid into a waste container 20 also stored in lower compartment 16. Preferably, the elevation of the aspiration tube is lower than that of the injection tube. As discussed above, one purpose of washing plate 4 is to remove any analyte or detection reagent that is unattached to the well, as well as any components of the sample that could interfere with the assay measurement.

While the plate is on the washer, robot arm 26 transfers a reagent reservoir containing a read buffer from shelves 22 to deck 40. After the plate is washed, robot arm 26 carries the washed plate to deck 40, where pipettor 34 transfers read buffer from the reagent reservoir to the plate. Robot arm 26 then transfers the plate to reader 36 where the assay measurement is carried out (e.g., in the case of an ECL measurement, by reader 36 applying a voltage to the electrodes in the wells to initiate the ECL reaction described above). The results are obtained by reader 36, and transferred to the operating computer stored in lower compartment 16. After completion, robot arm 16 returns the plates to shelves 14.

It is noted that the present invention is not limited to the steps described above. System 10 can execute any protocol involving any number of steps in any sequences involving the machineries and equipment described above.

According to the selected protocol, pipettor 32 may be used to carry out multiple pipetting steps on each of multiple plates in a run. An inventive aspect of the present invention is the use of pipettors employing disposable pipette tips, where the tips are cleaned between certain operations within a run and replaced at a lower frequency such as between runs. Additional inventive aspects relate to the specific cleaning procedures, reagents and subsystems used to clean tips that have been selected to maintain a high processing throughput while also providing negligible cross-contamination of samples. In one embodiment of the invention, pipette tips are washed between each cycle of operations (as defined below) carried out on an assay plate, to prevent cross-contamination of the wells in different assay plates. In some protocols, it may also be advantageous to wash the pipette tips between operations in one cycle, especially when the sequence of pipetting steps provides the possibility of cross-contaminating sample or reagent plates. Thus, types of carryover include sample carryover and reagent carryover. The tip-cleaning processes of the invention enable tip-cleaning to be carried out in less than 90 seconds (preferably, less than 60 seconds) while achieving an effective carry-over of less than 10 ppm, preferably less than 1 ppm or less than 0.1 ppm and preferably less than 0.01 ppm or 0.001 ppm, where the effective carry-over is the amount of a solution 1 transferred into a solution 2 after the two solutions are pipetted as numbered (1 then 2) using the same pipette tip. Effective carry-over may be determined, for example, by comparison of a test assay condition (using washed, reused pipette tips) to control assay conditions using fresh (unused) pipette tips for each sample. The control conditions may include running a Control Sample 1 in which a defined quantity of solution 1 is spiked into solution 2. The control conditions may also include running a Control Sample 2 that is solution 2, but unspiked with solution 1. The results for solution 2 under the test assay condition are compared to the difference in assay signals, e.g, analyte concentration, between Controls Sample 1 and Control Sample 2 under the control condition to determine the effective carry-over. See also Weibel et al., J. Lab. Automation 15:369-378 (2010). One of ordinary skill in the art understands how to adapt methods for measuring carry-over to different assay platforms and automated systems.

In one embodiment of the invention, the carryover of a protein analyte from a first sample to the following sample pipetted using the same tip is less than 1 ppm, preferably, when the analyte is measured by immunoassay. In another embodiment of the invention, the carryover of a nucleic analyte from a first sample to the following sample pipetted using the same tip is less than 1 ppm when analyzed by a nucleic acid hybridization or amplification assay.

To minimize effective carryover, the tip washing procedure preferably comprises: (i) one or more washing steps that physically remove materials on a tip that could lead to inaccurate assay results and (ii) an inactivation step in which the tip is exposed to an inactivation condition or reagent (e.g., solution) that inactivates any of such materials so as to reduce or eliminate the ability of these materials to affect assay results even if they are not fully removed by the washing steps. The inactivation step could include treatment of the tip with heat, with electromagnetic radiation (e.g., the use of UV light to inactivate nucleic acids in samples or reagent) and/or with a gaseous or liquid chemical reactants that react with materials that could cause carryover effects (e.g., the use of chemical oxidants such as bleach or hydrogen peroxide, acids or bases such as HCl or NaOH solutions, cross-linking agents such as formaldehyde and/or alkylating agents such as ethylene oxide). Preferably, the inactivation step comprises treatment of the pipette tip with a bleach solution. These conditions and reagents significantly reduce effective carryover of protein or nucleic acid analytes when pipetting a series of samples using the same disposable pipette tip. Using the tip washing procedures of the invention, disposable tips may be used to process 20 or more samples, preferably 100 or more samples, before requiring replacement with fresh tips.

Figure 4:
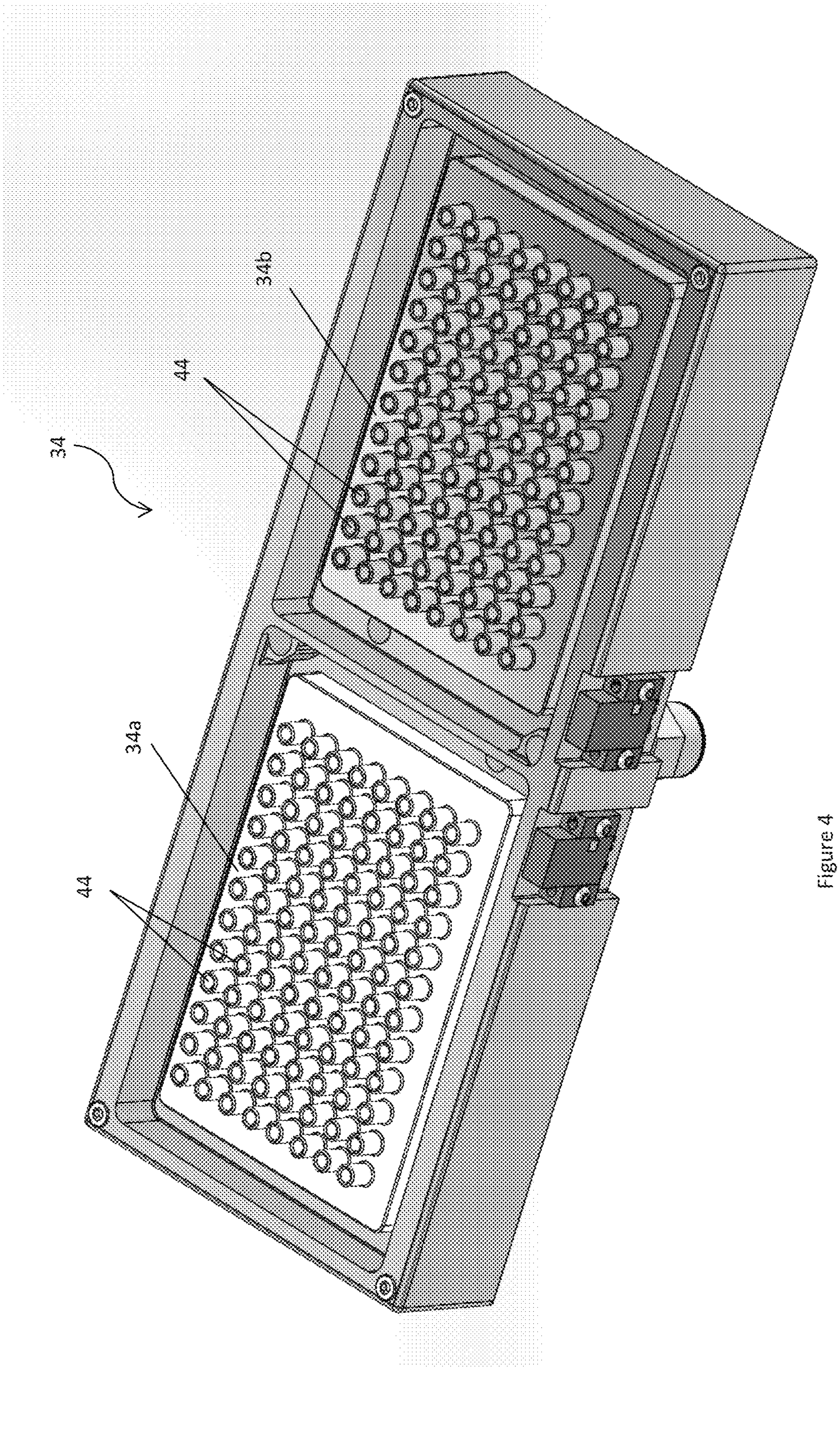
FIG. 4 is a perspective view of the pipette tip washing manifolds.
Figure 5:
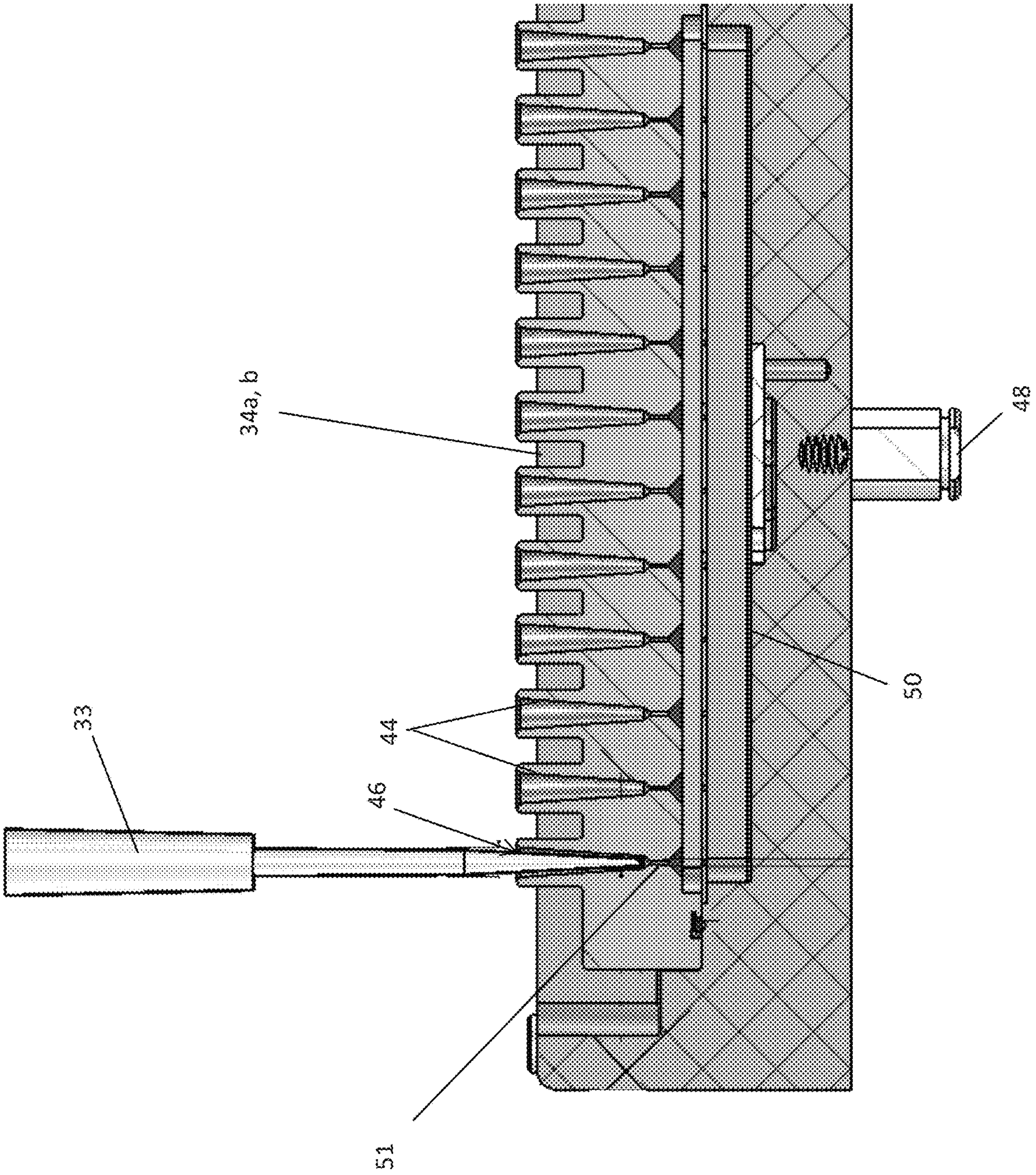
FIG. 5 is a cross-sectional view of a number of chimneys in the washing manifolds of FIG. 4 with an exemplary pipette tip.
Figure 6:
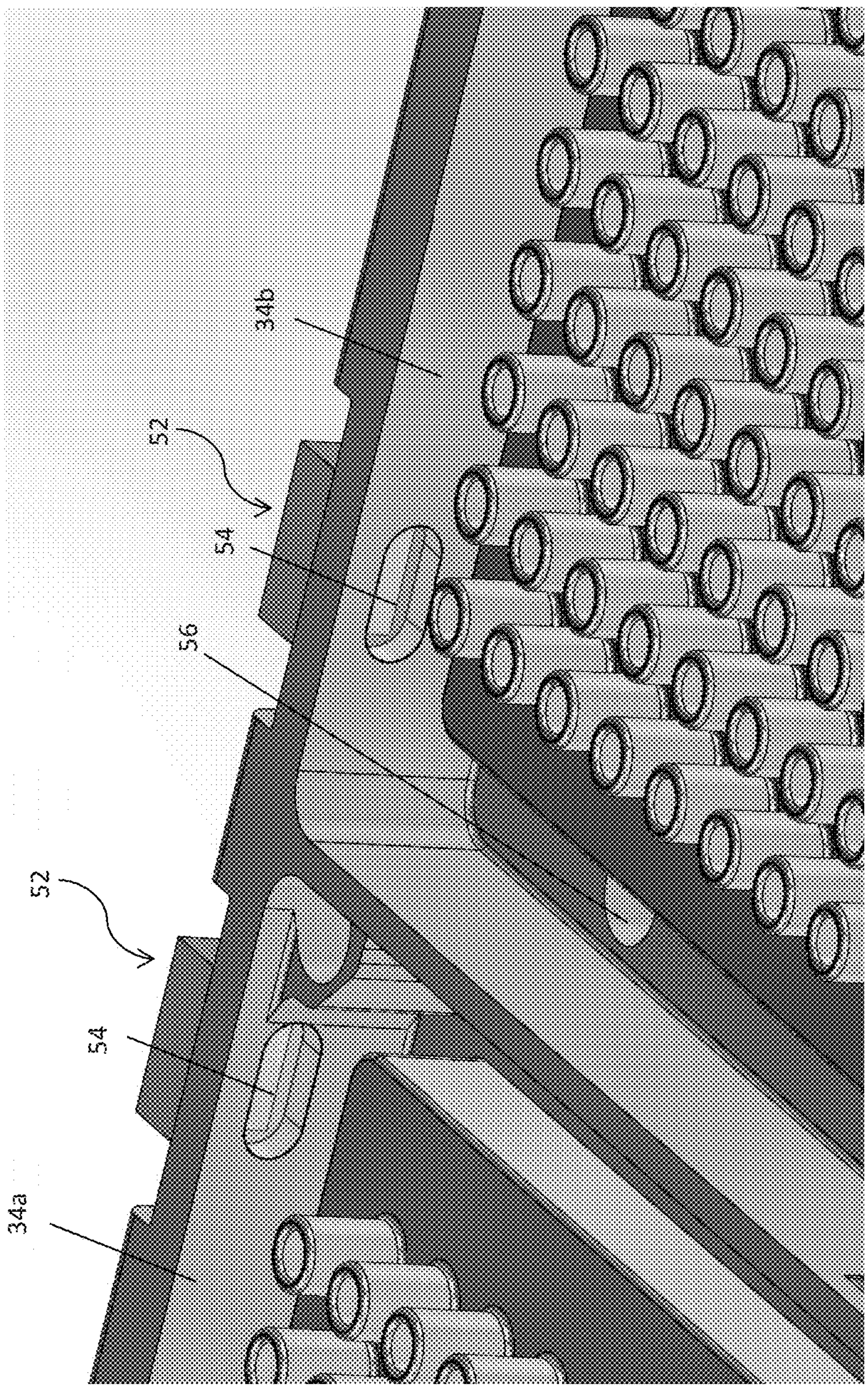
FIG. 6 is a close-up view of the washing manifolds of FIG. 4.

One embodiment of the tip washing procedures of the invention uses the following process. To clean the pipette tips 33, robot arm 26 removes an inactivation reagent reservoir (e.g., a reservoir containing a bleach solution as in the description below) from shelves 22 and places it securely on plate pipette deck 40. Referring to FIGS. 4-6, pipette tip washing manifold 34 preferably has two manifolds for physically washing the pipette tips. First manifold **34*a* preferably uses a mixture of water and surfactants to rinse the pipette tips and second manifold 34*b* preferably uses deionized water. Both manifolds have a plurality of chimneys 44 that match the number of pipette tips 33 on pipettor 32. Pipettor 32 is supported by gantry 42 and is movable in three directions in order to move along deck 15. In one embodiment, pipettor 32 is positioned over either manifold 34*a* or 34*b* and is positioned so that pipette tips 33 are located between chimneys 44, in other words pipette tips 33 are mis-aligned with the openings of chimneys 44. Next, any remaining contents inside pipette tips 33 are discharged on to the manifold without going into and contaminating chimneys 44. Thereafter, pipettor 32 is moved to a position above the bleach solution reservoir and is inserted into the bleach solution. A first volume of bleach solution is aspirated into pipette tips. Preferably, this first volume is larger than the volume of any prior sample or reagent(s) so that the bleach solution migrates a sufficient height inside pipette tip 33 to overlap a previous height of sample or reagent(s). The bleach solution is then expelled from pipette tips 33**. A bleach solution can be reused a number of times, e.g., 10 times, until a fresh bleach solution reservoir is needed. Optionally, the steps associated with treatment with bleach (i.e., the inactivation steps) may be omitted for pipetting steps where the effect of carryover on the assay is likely to be small.

Thereafter, pipettor 32 is moved to a position above first manifold 34*a* and pipette tips 33 are aligned directly over chimneys 44. As best shown in FIG. 5, pipettor 32 dips pipette tips 33 into chimneys 44 but maintains a gap 46 between tip 33 and chimney 44. Washing liquid with an amount of surfactant from a container located below in lower compartment 16 is pumped into chimneys 44 from the bottom through conduit 48 and manifold 50 to be distributed to chimneys 44. Optionally, a flow restrictor 51 is positioned upstream of each chimney 44 to ensure uniform fluid flow into gap 46 from manifold 50 below. A flow restrictor can be a section of reduced diameter. A second volume of water and surfactant is aspirated into pipette tip 34, wherein this second volume is larger than the first volume. Additional water and surfactant is pumped through gap 46 to wash the outside of pipette tips 33. To maximize this outer flow of water, gap 46 preferably has a constant clearance. In other words, the outer shape or surface of pipette tip 33 matches the inner surface of chimney 44 to maintain a constant clearance between tip 33 and chimney 44. Preferably, this clearance is between 0.25 mm and 1 mm, more preferably between 0.5 mm and 0.75 mm.

After being washed with the surfactant solution in first manifold 34*a*, pipettor 32 moves pipette tips 33 to second manifold 34*b* and the same rinsing is repeated but with deionized water. A third volume of deionized water is aspirated into pipette tips 33, wherein the third volume is greater than the second volume. In one example, the first volume is about 75 ml, the second volume is about 100 ml and the third volume is about 125 ml.

To clean pipette tips 33, both the inside and the outside of the pipette tips should be cleansed. For internal washing, the amount of aspirated volume at each washing step should be progressively larger with progressively "cleaner" solution, i.e., closer to clean water. For example, in the discussion above, the aspirated volumes progressively increases from the first volume to the third volume and from a bleach solution to a soapy solution (with surfactant) to deionized water. Alternatively, the bleach solution may be omitted. The washing is separated into at least two reservoirs (34*a*, 34*b*). A rough wash in reservoir 34*a* and a fine wash in reservoir 34*b*. Within each reservoir, contaminants are effectively removed iterative wash cycles, i.e., preferably using a directional flow. For external washing, pipette tips 33 are located proximate narrow gaps 46 to get more shear force from the flow from manifold 50. Flow restrictions 51 may be positioned upstream of gap to control and increase the flow through gaps 46.

This washing process allows disposable pipette tips to be re-used in system 10. Fresh disposable pipette tips are installed onto pipettor 32 at the beginning of each run, and can be used throughout the run and are disposed at the conclusion of a run.

Referring to FIG. 6, first and second manifold 34*a* and 34*b*, preferably has level sensor 52 positioned on a wall thereof. In one embodiment, level sensor 52 is an optical reflectivity sensor that emits an IR (infrared) beam toward a transparent window 54, which preferably is acrylic. The index of refraction of window 54 is close to that of the wash liquid but is different than that of air. When air is behind window 54, the difference between the indices of refraction between window 54 and air is sufficiently high to cause a higher amount of IR to reflect by window 54. When washing liquid is behind window 54, the difference of indices of refraction between window 54 and washing liquid is sufficiently similar so that more IR is transmitted through window 54. Sensor 52 is capable of detecting higher IR transmission indicating that the liquid level is at window 54. This would signal to the operating computer to shut down the pump to stop the flow of washing liquid, until the liquid is drained through drain holes 56. Drain holes 56 are connected to a waste container located in lower compartment 16.

Advantageously, level sensor 52 can be used to establish a constant fill level within pipette tip washing manifold 34. The pump can be shut off and drain holes 56 can be pinched when sensor 52 senses that the level reaches window 54. This fill level is known to the operating computer, and in the event that droplets of waste are hanging off of pipette tips 33, pipettor 32 can position pipette tips 33 away from chimneys 44 and lower tips 33 to an elevation above the fill level but sufficient for the drops of waste to touch the liquid. This allows the waste droplets to be transferred to the liquid in washing manifold 34 without touching the pipette tips to this liquid, which may have been previously used to wash pipette tips 33 and may contain contaminants.

According to another aspect of the present invention, an advantage of enclosing the machineries inside enclosure 12 is that the temperature and/or humidity inside enclosure 12 can be controlled and the evaporation of reagents and other liquids can be minimized. Enclosure 12 does not need to be sealed from the environment; however, the inside of upper compartment 14 does not actively exchanging air with outside environment. Upper compartment 14 is enclosed by a top surface, side surfaces, back surface and deck 15. The front surface comprises one or more sliding or hinged doors. In certain applications, it is desirable to maintain the temperature within upper compartment 14 between about 23° C. and about 27° C. and within ±1° C. at certain selected preset temperature within this temperature range.

Figure 7:
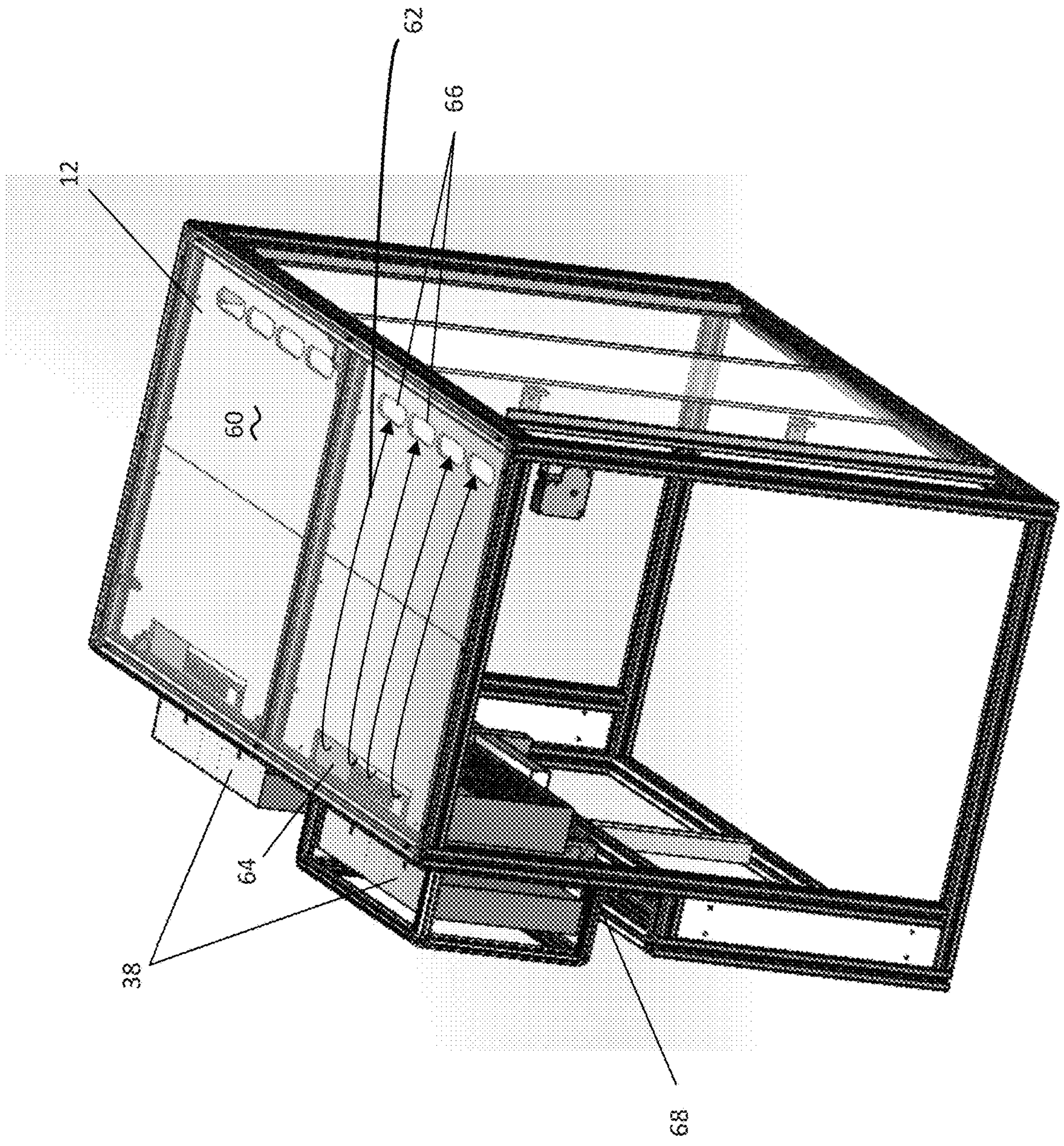
FIG. 7 is a perspective view of the enclosure of the system of FIGS. 2 and 3 with elements omitted for clarity showing a flow plenum.

Referring to FIG. 7, another inventive aspect of the present invention relates to the controlled airflow within upper compartment 14. Since a number of machineries and other objects are present on deck 15, they can obstruct the air flow and redirect the air flow in an uncontrolled fashion. Thermoelectric coolers 38 generally take in air inside upper compartment 14 horizontally at about their center, cool/warm the air and discharge air vertically at their top and their bottom. FIG. 7 illustrates enclosure 12 with the machineries and other components omitted for clarity. The top surface of enclosure 12, shown at reference number 58 in FIG. 2, and deck 15 also omitted for clarity. Below top surface 58 of enclosure 12, a second top surface 60 is positioned below top surface 58 to create a flow plenum 62 at the top of upper compartment 14. Preferably, second top surface 60 is spaced at a sufficient distance from top surface 58 to allow the discharged air to flow through. The dimensions of flow plenum 62 can be adjusted smaller to speed up the air flow or larger to slow it down. Second top surface 60 has at least one ingress 64 located proximate to the top discharge of thermoelectric cooler 38, and at least one egress 66 near the front of upper compartment 14. As shown, the top discharged air enters flow plenum 62 at ingress 64 and flows along the plenum until it reaches egress 66 near the front of upper compartment and is forced to flow downward to modulate the temperature of the machineries before flowing back into the thermoelectric cooler at its intake. Without flow plenum 62, the flow pattern from the top discharged air may not reach the front portion of upper compartment 14, because the discharged air may bounced off of top surface 58 toward the horizontal intake without travelling to the front of upper compartment 14.

Figure 8:
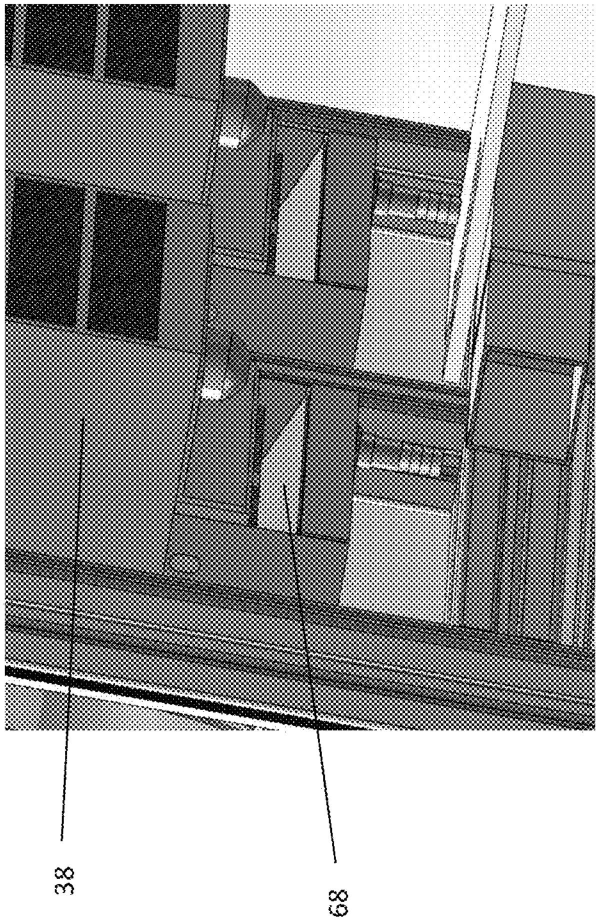
FIG. 8 is a close-up view of a flow diverting plate shown in FIG. 7.

Additionally, an inclined flow diverter 68 as shown in FIGS. 7 and 8 is positioned directly below the bottom discharge of thermoelectric coolers 38 to divert the flow along deck 15 to direct the air flow toward the front of upper compartment 14 and then upward and back toward the thermoelectric coolers' horizontal intake. In another embodiment, a second flow plenum 62 can be provided with deck 15, whereby a bottom surface is positioned below deck 15 and ingress 64 and egress 66 are provided on deck 15.

The modified air flows at the top and/or at the bottom of upper compartment 14 result in longer airflow paths from the top and bottom discharges of thermoelectric coolers 38 back to their horizontal center intakes. The longer airflow paths provide more efficient distribution of airflow throughout the upper compartment and reduce temperature gradient within the enclosure and to maintain the temperature difference within upper compartment 14 to be within ±1° C.

Protocols

ECL immunoassay system 10 is capable of performing any number of assaying protocols. Preferably, the assay protocol for processing each plate is broken down into a series of timed processing cycles of equal duration, where each cycle involves the processing of a single plate on deck 15 and the different cycles carried out on individual plates may be separated by plate incubation periods. This approach can provide extremely high-throughput processing, while maintaining precise control of the timing of assay steps and greatly simplifying the scheduling of individual automated operations. As long as each cycle has a duration of N minutes (which means the operations or steps within a cycle take less than N minutes) and the incubation time between any two adjacent cycles for a given plate is at least Y minutes, then system 10 can batch Y/N plates in a run without having to access two plates at the same time while maintaining consistent timing for all the assay processing and incubation steps on all the plates.

In one embodiment of this "timed cycle" approach, the individual cycles that make up the processing sequence for an assay protocol, are created by modifying a generic multistep cycle by omitting steps that are not required in that specific cycle and, for steps involving fluid transfers, by specifying the number of volumes of the transfers. The modified cycles are achievable within the time duration of the full generic cycle and do not require any modification to the overall scheduling of cycles.

Figure 9A:
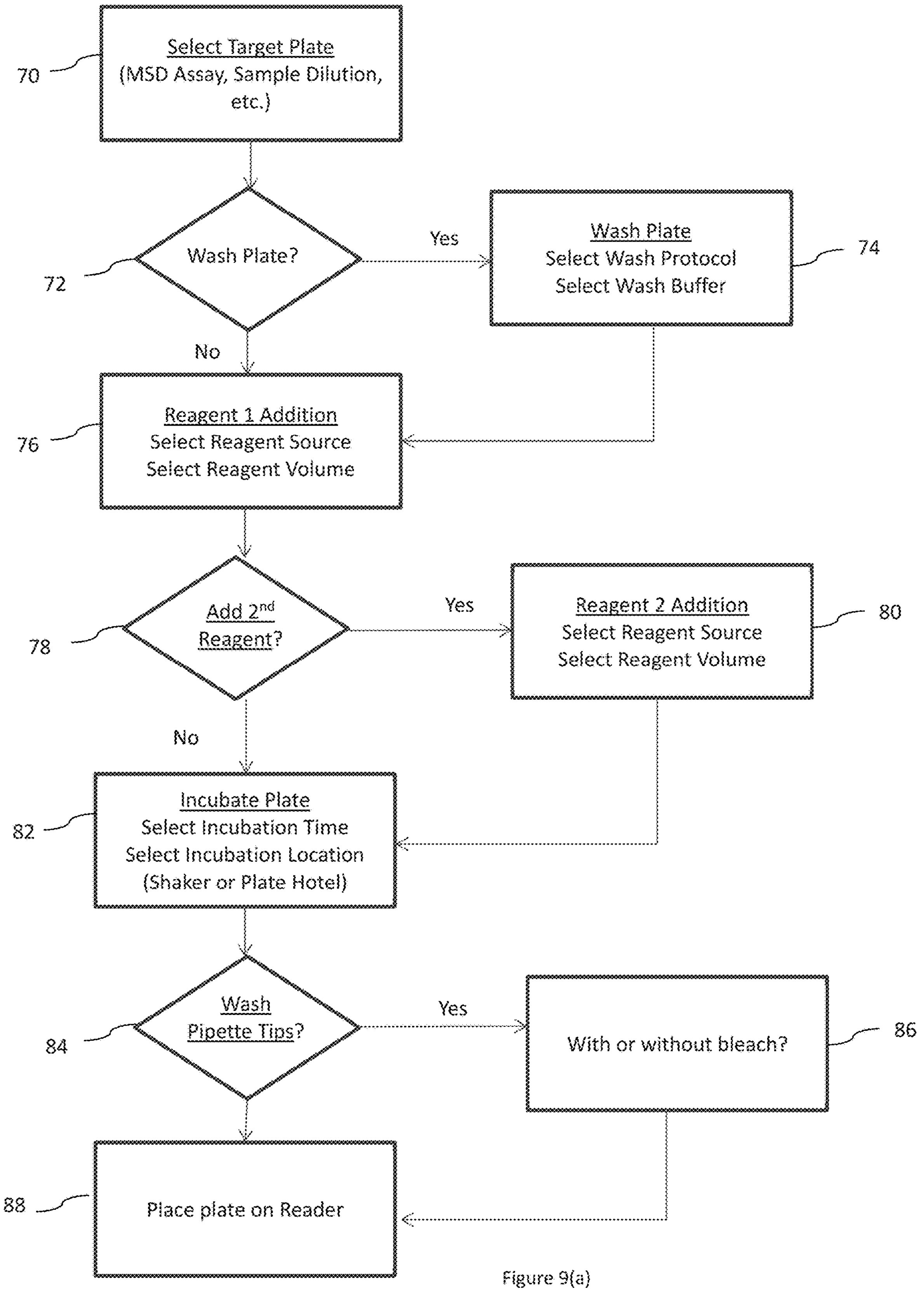
FIGS. 9(*a*)-(*b*) are a flow charts of exemplary methods for operating the inventive system.
Figure 9B:
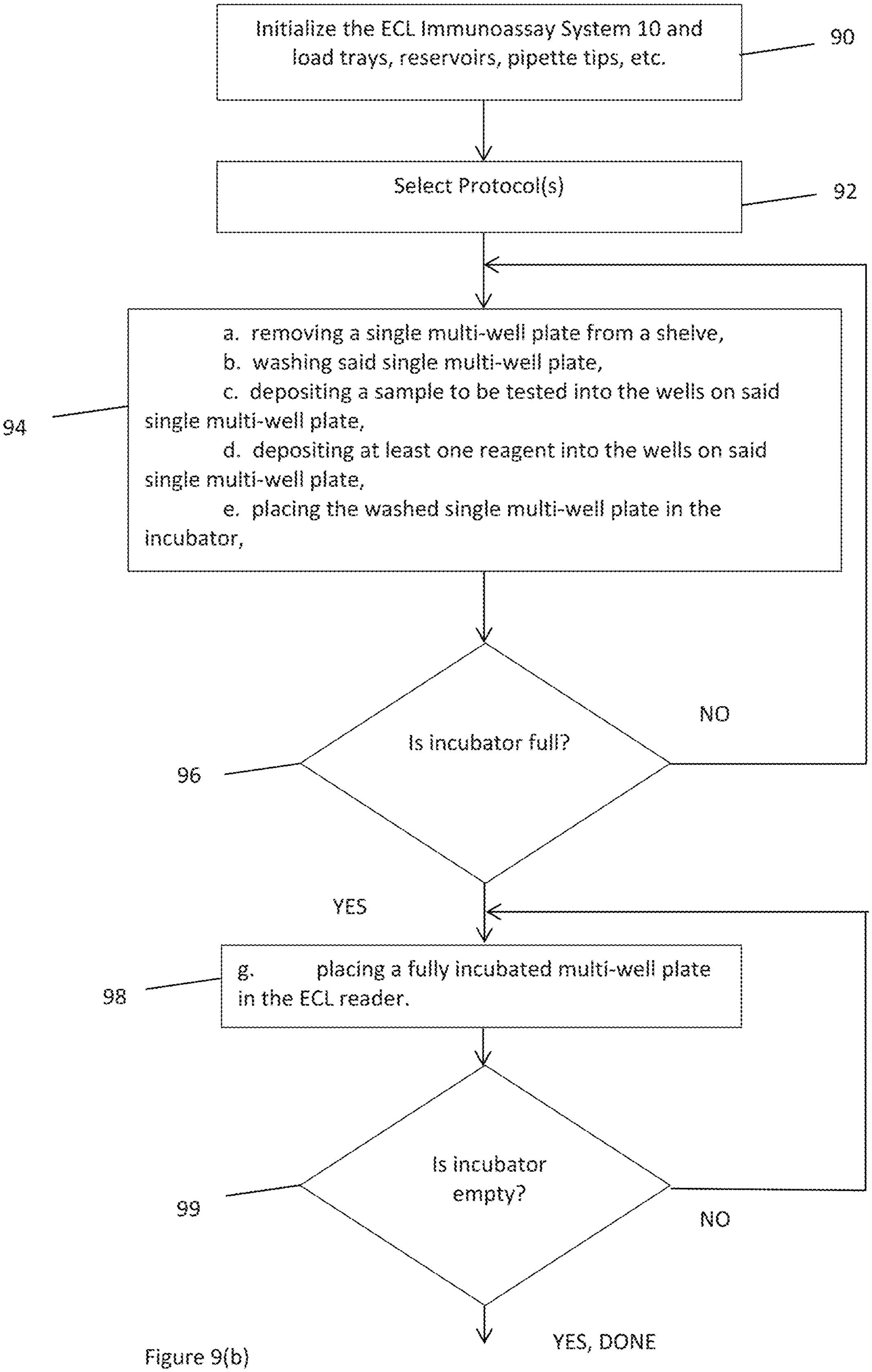
Figure 10A:
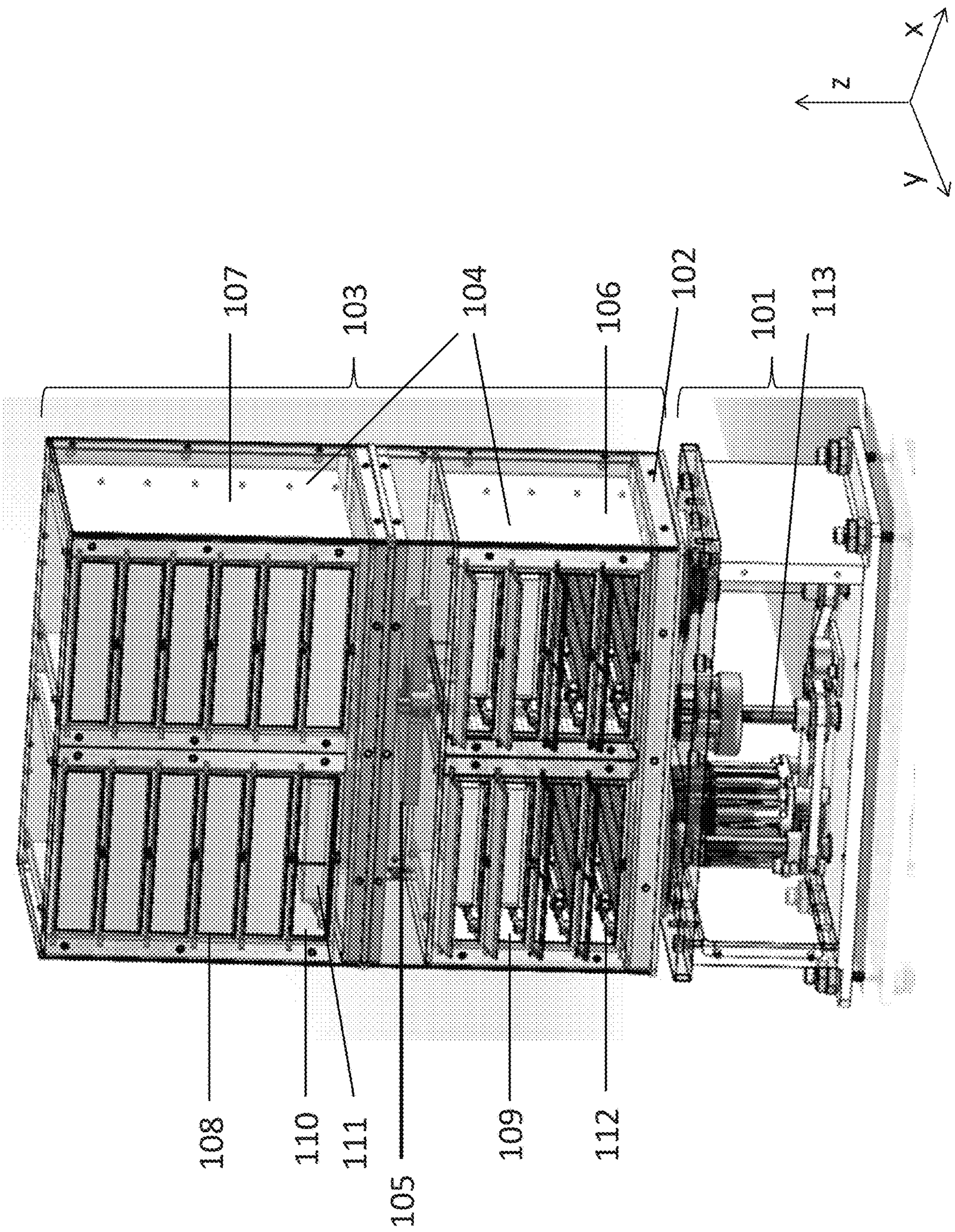
FIGS. 10(*a*)-(*b*) are perspective front views showing detailed views of the shaker apparatus with portions of the housing omitted to show the internal mechanisms.
Figure 10B:
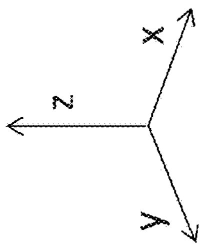
Figure 10B:
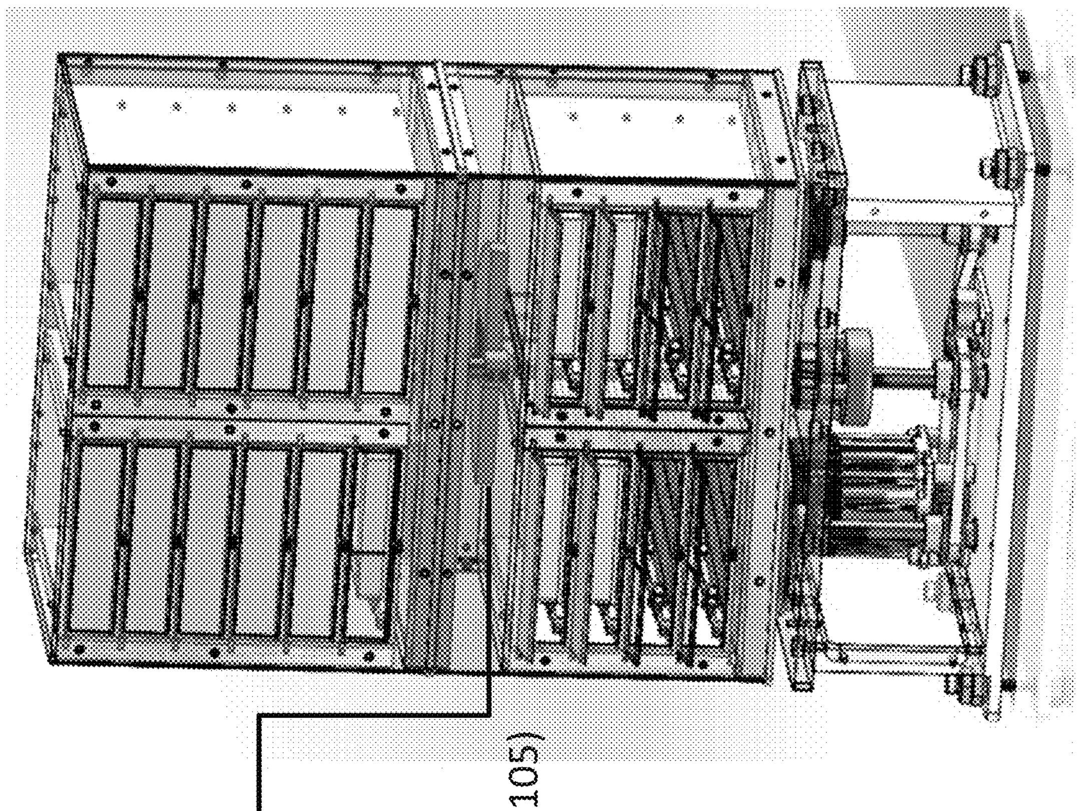
Figure 10C:
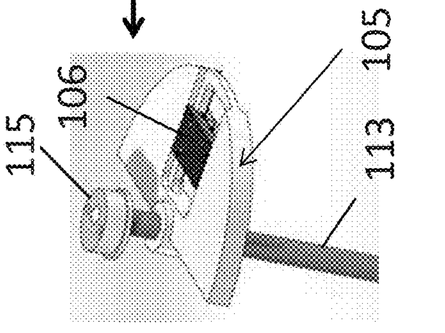
Figure 10D:
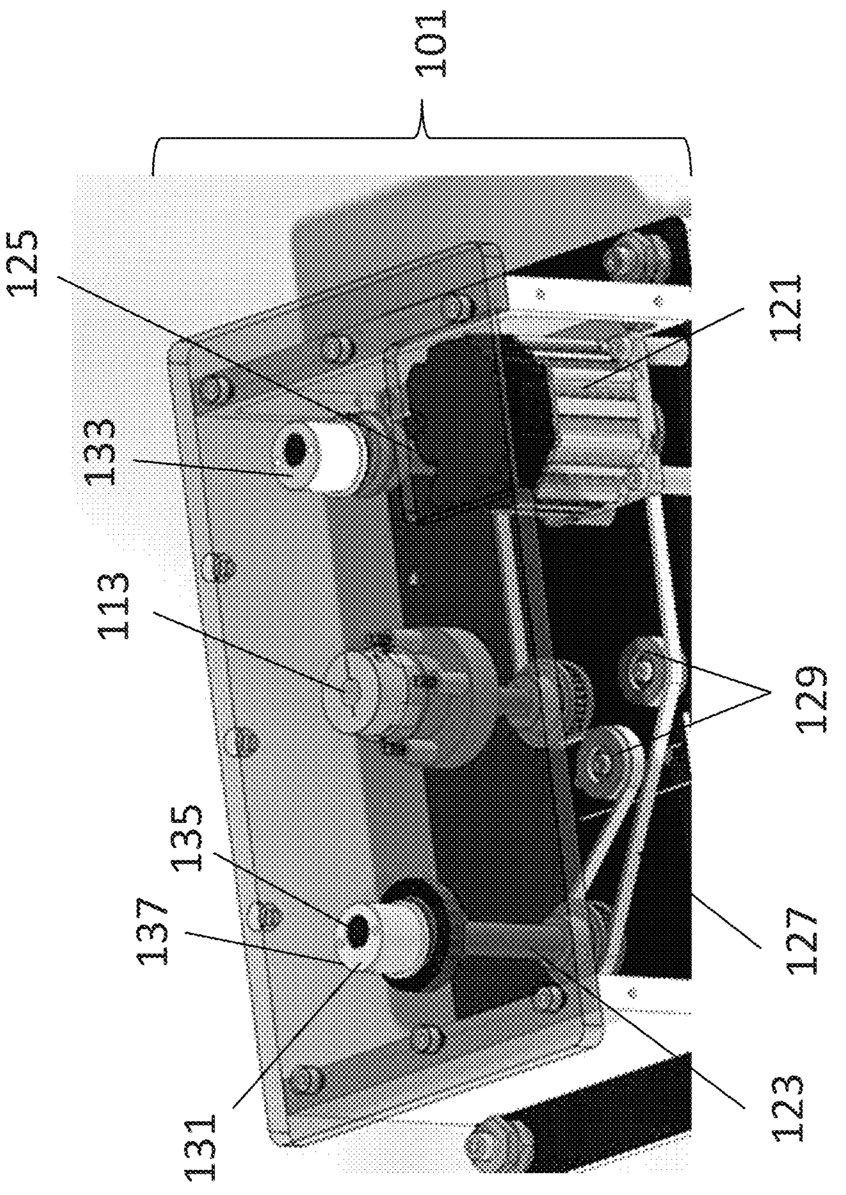
Figure 11B:
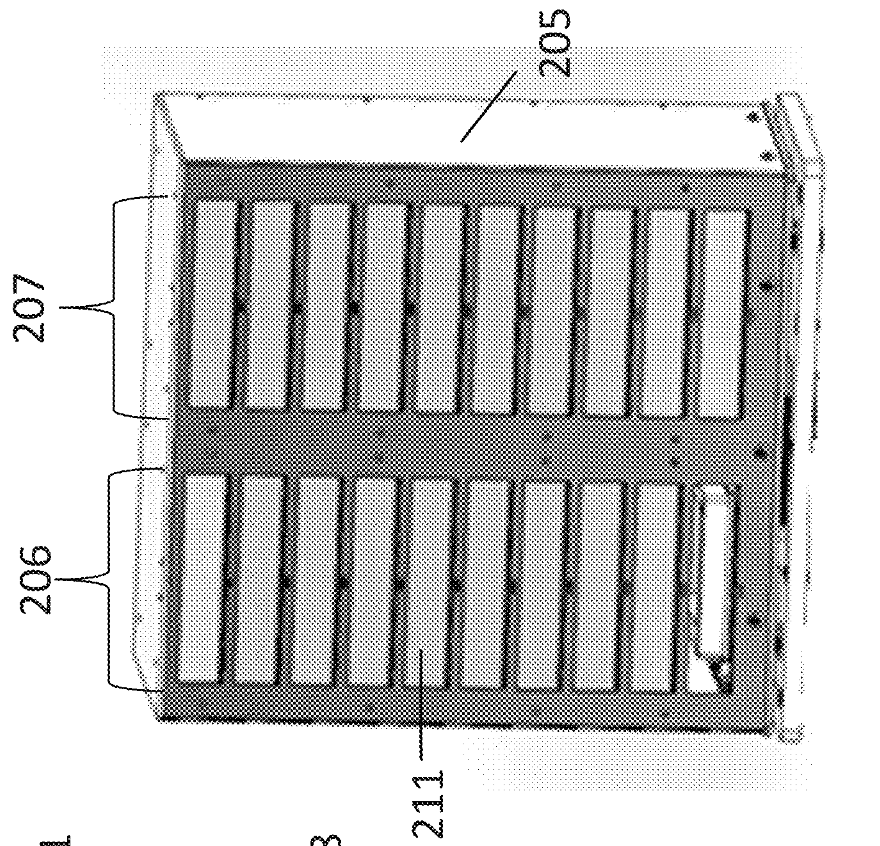
FIGS. 11(*a*)-(*i*) show detailed views of the storage assembly including various alternative configurations of sets of vertically aligned storage units within the storage assembly (FIGS. 11(*c*)-(*i*)).
Figure 11A:
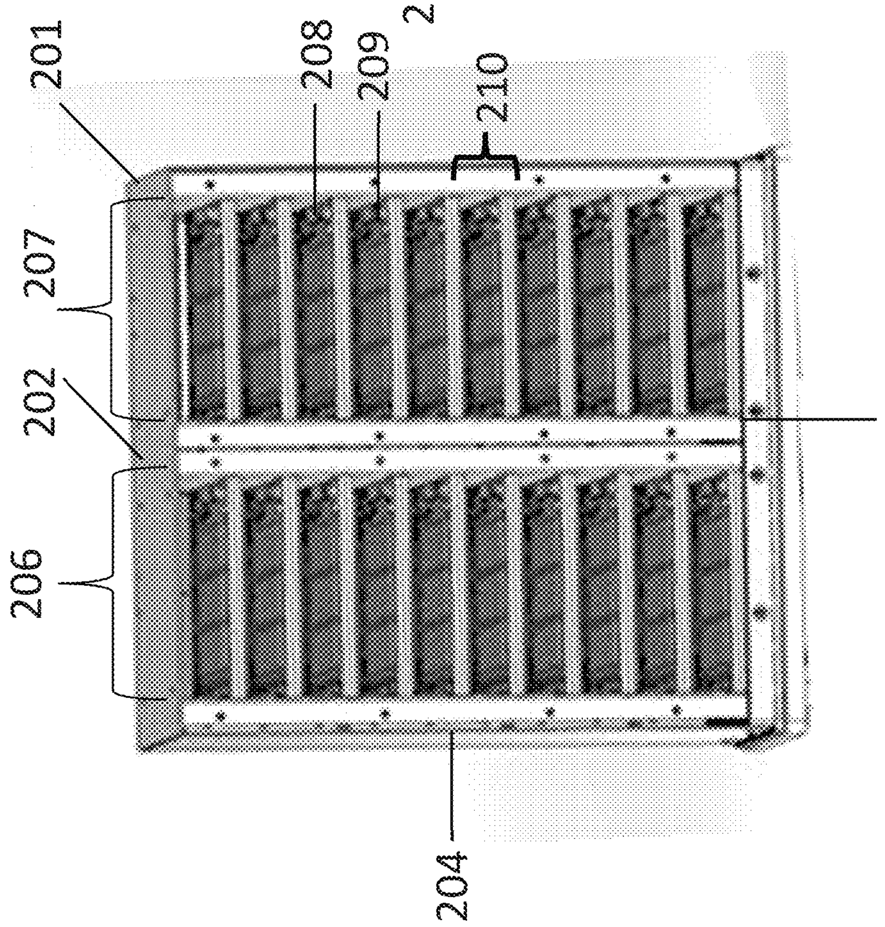
Figure 11C:
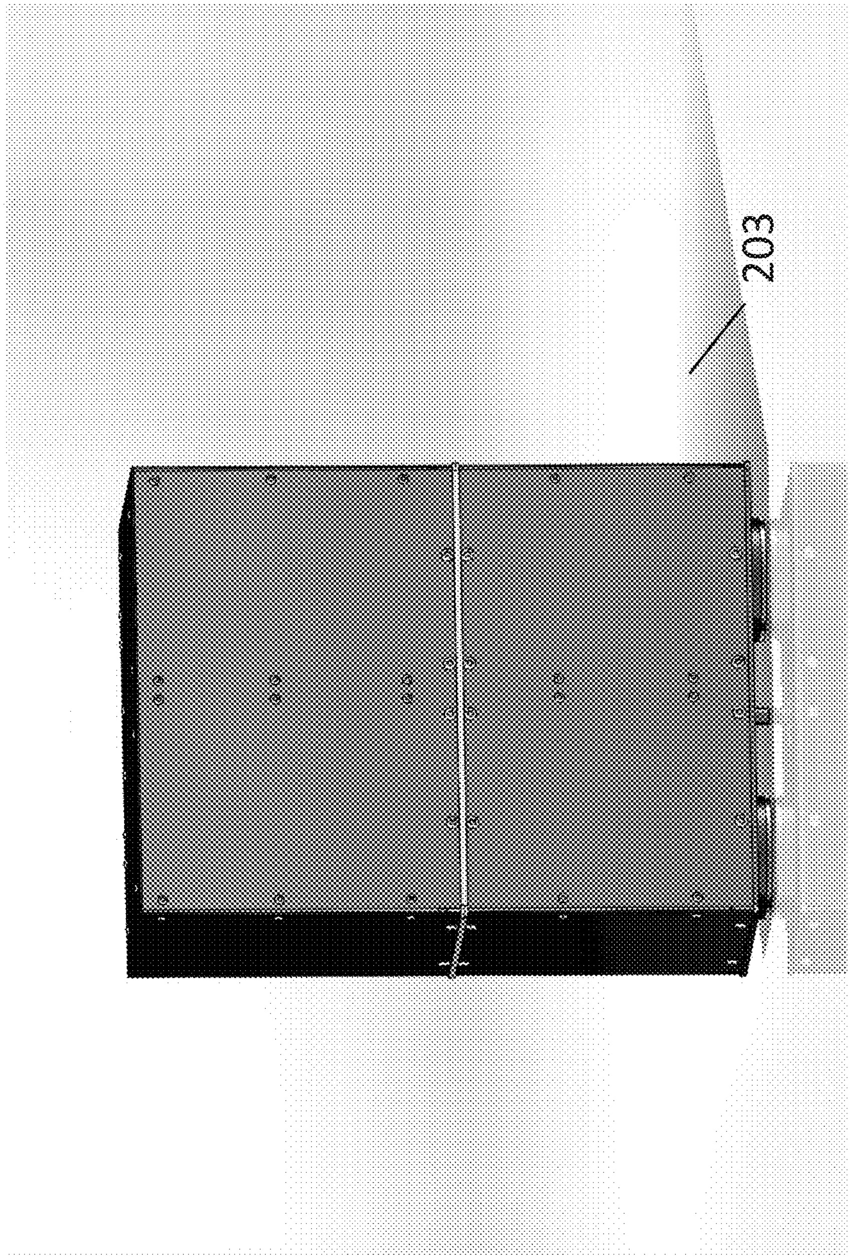
Figures 11G, 11H, 11I:
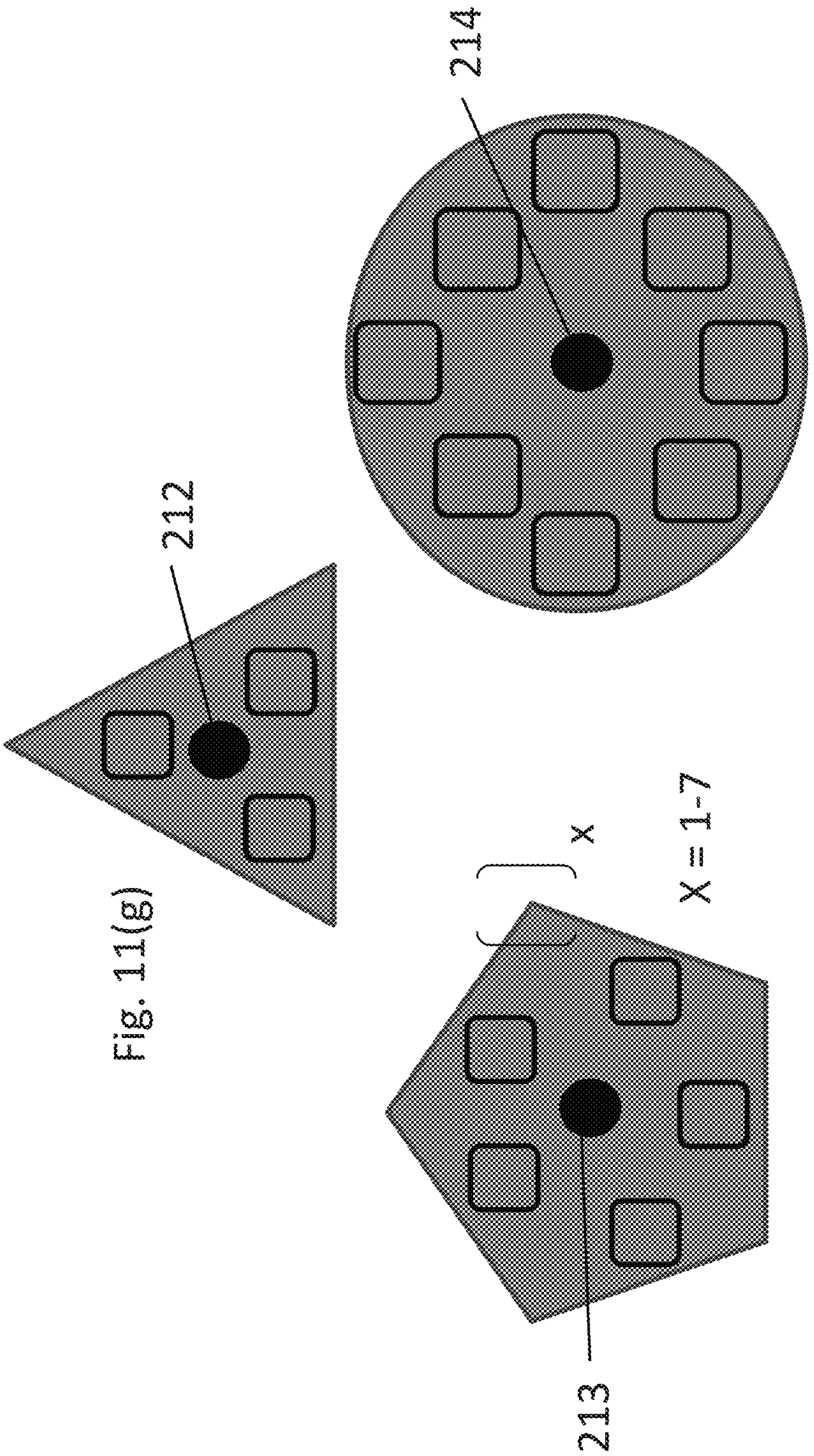

An exemplary flow chart of one generic cycle is illustrated in FIG. 9(*a*), as are some of the opportunities for modifying the cycle to produce assay specific cycles. In step 70, a target plate is selected. In step 72, a decision whether to wash the plate is made. If YES, then in step 74, a wash protocol is selected and a wash buffer is selected. After step 74 or if the decision in plate washing from step 72 is NO, then the protocol proceeds to step 76, where reagent (or sample) is added. A reagent (or sample) source and a reagent (or sample) volume are selected. Thereafter, another decision whether to add a second reagent (or sample) is made in step 78. If YES, then in step 80, another reagent (or sample) source and volume are selected. After step 80 or if the decision from step 78 is NO, then the protocol proceeds to step 82 where the plate is incubated and stirred. An incubation time and an incubation location, e.g., shaker 28 or shelves 22, are selected. Next, in step 84, a decision whether to wash the pipette tips is made. If YES, another decision whether to wash with a inactivating solution such as bleach or not is made at step 86. After step 86 or if the decision from step 84 is NO, then the protocol proceeds to step 88 and place the plate on reader 36.

In one example, one assay protocol may have the following cycles, created by modifying the generic cycle of FIG. 9(*a*), with the following steps/operations:

Cycle 1. Pull assay plate and blocking reagent reservoir from shelves 22, add blocking reagents to plate using pipettor 32 and put plate in shaker 28.

Cycle 2. Pull assay plate from shaker 28 and sample plate from shelves 22, wash assay plate at plate washer 30, add samples to plate using pipettor 32, put plate on shaker 28.

Cycle 3. Pull assay plate from shaker 28 and detection reagent reservoir from shelves 22, wash assay plate, add detection reagent to plate using pipettor 32, put plate on shaker 28.

Cycle 4. Pull assay plate from shaker 28 and read buffer reservoir from shelves 22, wash assay plate, add read buffer to plate using pipettor 32, place plate of reader 36 for analysis. In this example, each cycle takes 3 minutes or less to run, and if the incubation time on shaker 28 is 60 minutes, then system 10 can run batches of 20 multi-well plates without interference between plates.

In another example, the system may be used to run protocols that include an incubation that is short or comparable in duration to the duration of a cycle, e.g., incubation times in the range of 10 seconds to six minutes. This protocol is suitable for running assays for high abundance of analytes with short incubation instead of requiring dilutions. For incubations that are short relative to the length of a cycle, the incubation may be carried out as a step within the cycle. In this case, the plate may be left on the deck (either without shaking during incubation or using the pipettor to mix through up and down pipetting) or the plate may be transferred to the shaker, incubated and transferred back to the deck within the time frame of a single cycle. In the case where the incubation time is a multiple M of the cycle time N (i.e., the incubation time=M×N), an interleaved process can be used that interleaves the pre-incubation processing steps (comprised within a pre-incubation subcycle of duration A) and the post-incubation processing steps (comprised within a post-incubation subcycle with duration B), where A+B=N (the total time for an individual cycle). In this case, a processing cycle for the interleaved process may comprise (i) process a plate in the batch using the pre-incubation subcycle or, if no plate is available (e.g., all the plates have already undergone the pre-incubation subcycle) then idle for time A and (ii) process a plate in the batch that has completed the M×N time incubation using the post-incubation subcycle or, if no plate is available (e.g., no plates have completed the M×N incubation) then idle for time B. Using this interleaved approach, it is possible to continuously process plates and there is no upper limit in batch size. If the assay process comprises an additional long incubation step of time Y, as described above for the timed cycle approach, then the length of the long incubation step will determine that batch size that can be run during the protocol.

In yet another example, system 10 can be operated as illustrated in FIG. 9(*b*). In step 90, system 10 is initiated, wherein the consumables such as plates, reservoirs, pipette tips, etc. are loaded, as described above. In step 92, a protocol is selected by the operator. In step 94, a first single multi-well assay plate is processed, using a first processing cycle that includes one or more of exemplary processing steps (a)-(f) are performed.

a. removing a single multi-well tray from a shelve,
b. optionally, washing said single multi-well tray,
c. depositing a sample to be tested into the wells on said single multi-well tray,
d. depositing at least one reagent into the wells on said single multi-well tray,
e. optionally, washing said single multi-well tray to remove remaining analytes;
f. placing the optionally washed single multi-well tray in the incubator, The first processing cycle repeated with additional single multi-well assay trays until the incubator is full as indicated in step 96, i.e., (h) repeating steps (a)-(f) with another single multi-well tray until the incubator is full. The period of incubation in this example is the sum of the time to fill the incubator with multi-well trays. After the incubator is filled with processed trays, step (g), as illustrated in step 96, the first tray, which is now fully incubated, is removed and, optionally, processed using a second processing cycle 94 that includes one or more of steps (a)-(f). The second processing cycle, if used, is then repeated with additional single multi-well trays until the incubator is full. Similarly, additional processing cycles 94 may also be carried out on the batch of plates as needed for a specific assay protocol. The final processing cycle will also comprise processing step (h) (shown as step 98 in FIG. 9*b*) in which the assay tray is transferred to a plate reader (e.g., an ECL tray reader) for analysis. The final cycle is repeated until all assay trays are placed in the reader in step 99 and analyzed. The number of multi-well trays stored in the incubator is equal to the incubation period divided by the time to complete the longest of the processing cycles (i.e., steps (a)-(f) and, in the final cycle, (h)).

The method illustrated in FIG. 9(*b*) can be modified by first determining the number of multi-well trays that can be processed and stored in the incubator during the incubation period, and then processing the trays according to processing steps (a)-(f). The system can process the remaining trays, and after the first tray is fully incubated the trays are moved to the reader for ECL analysis on a first-in-first-out basis.

Any number of protocols can be designed based on the teachings herein by those of ordinary skill in the art. The present invention is not limited to any particular protocol.

Descriptions of System 10's Components

The machineries and equipment shown and described above, and particularly in FIGS. 2 and 3 can be specifically designed or can be commercially purchased. Shelves 22 are preferably custom built for the applications intended. Bar code reader 24 can be a commercial off-the-shelf component. Robot arm 26 can also be a commercial off-the-shelf component. Plate washer 30 can also be a commercial off-the-shelf component, and is available from Biotek, Inc. Reader 36 can also be a commercial off-the-shelf component, and is available from Meso Scale Diagnostics, Inc. as MESO QuickPlex SQ 120 Reader. This Reader is described and claimed in commonly-owned pre-grant U.S. patent application publication no. US2014/0191109, which is incorporated herein by reference in its entirety. Multichannel pipettor 32 and thermoelectric coolers 38 are also commercial off-the-shelf components. Pipette washing manifolds 34 can be specifically built, or purchased and modified to improve the washing effectiveness. Gantry 42 is preferably specifically built for system 10.

Shaker 28 can be a commercial off-the-shelf component; however, in the embodiment of system 10 discussed above, shaker 28 is inventive and described and claimed in commonly owned provisional application entitled "Consumable Shaking Apparatus" filed on Apr. 6, 2015 bearing Ser. No. 62/143,557, which is incorporated herein by reference in its entirety. Relevant portions of this earlier provisional application are reproduced below.

A shaker and incubation apparatus 28 is shown in FIGS. 10(*a*)-1(*d*). The apparatus includes an orbital shaker assembly (101), including a horizontal orbiting platform (102), and an assay consumable storage assembly (103) positioned on the platform (102). The storage assembly (103) includes a shelving subassembly (104) and a counterweight (105) positioned within the storage assembly at a height or plane that substantially corresponds to the center of mass of the orbiting components of the apparatus, i.e., the storage assembly and the orbiting platform. The shelving subassembly includes a plurality of sets of vertically aligned storage units. The apparatus depicted in FIGS. 10(*a*)-1(*b*) includes four sets of vertically aligned storage units (106-109). Each storage unit (110) is sized to accommodate an assay consumable (111) and includes a latching mechanism (112) to secure the consumable within the storage unit and to ensure that each consumable positioned within the subassembly is subjected to the same orbital shaking momentum, velocity, and direction.

Examples of assay consumables suitable for use with the invention include, but are not limited to, vials, flasks, beakers, assay cartridges and cassettes, microtitre plates, e.g., multi-well plates, slides, assay chips, lateral flow devices (e.g., strip tests), flow-through devices (e.g., dot blots), solid phase supports for biological reagents and the like. In certain embodiments, test sites in the assay consumable are defined by compartments in the assay consumable, e.g., wells, chambers, channels, flow cells and the like. In a specific embodiment, the assay consumable is a microtitre plate, e.g., comprising 6, 24, 96, 384 or 1536-wells. More particularly, the assay consumable is a 96-well microtitre plate.

Referring to FIGS. 10(*a*) and 1(*d*), the orbital shaker assembly 101 includes a rotating shaft (113) that extends from the orbital shaker assembly (101) into the assay consumable storage assembly (103) in the vertical Z-axis. The counterweight (105) is operatively connected to shaft (113) at or near the centroid plane or the plane that includes the center of mass of the assay consumable storage assembly (103). Top eccentric (115) is operatively connected to the top of the rotating shaft (113) and to a chassis or surface of assay consumable storage assembly (103), discussed further below.

Referring to FIG. 10(*d*), the orbital shaker assembly (101) has driving motor (121) connected to rotating shafts (113), (123) and (125) by means of a belt (127). Preferably, the belt (127) is grooved or is a timing belt. One or more pulleys (129) are positioned to ensure that the shafts are driven and are driven at substantially the same rotational speed. Shafts (123 and 125) are operatively connected to first bottom eccentric (131) and second bottom eccentric (133). Bottom eccentrics (131, 133) are operatively connected to horizontal orbiting platform (102) which supports assembly (103) or operatively connected directly to assembly (103), and as stated above top eccentric (115) is operatively connected to a chassis or surface of assay consumable storage assembly (103) at or near a plane that includes the center of mass of assay assembly (103).

The eccentrics (115, 131 and 133) are cylindrical components positioned about the rotating shafts (113, 123 and 125, respectively) having an inner and outer diameter (125 and 137, respectively) that do not share the same centerline. The rotating shafts are received within the inner diameter of the eccentrics, and the eccentrics are received within ball bearing receivers on horizontal orbiting platform (102), which supports the assay consumable storage assembly (103) as best shown in FIG. 10(*a*), and/or within ball bearing receiver adapted to receive top eccentric (115). The distance between the centerlines of the inside and outside diameters of the eccentric determines the orbital radius of the apparatus. For example, in the embodiment shown in FIG. 10(*c*), the distance between the centerlines of the inside and outside diameters is 2 mm; therefore the orbit radius is 2 mm, but this configuration can be adjusted without departing from the spirit or scope of the invention. In one embodiment, all rotating components (e.g., the motor, drive shafts, and counterweights) rotate at the same speed and in the same direction.

In another embodiment, at least two bottom eccentrics (131 and 133) are attached to the horizontal orbiting platform (102) to minimize or preferably prevent the assay consumable storage assembly (103) from rotating about a single rotating axle. Preferably top eccentric (115) is used to minimize or prevent the shaft (113) from orbiting—shaft (113) should primarily rotate or only rotate. Additional bottom and top eccentrics can be used. Similarly sized eccentrics are used on the bottom mounting plate and on top of shaft (113) to mechanically constrain the shaft vertically, in other words to help ensure that the entire assay consumable storage assembly (103) orbits uniformly about the vertical Z axis. All the eccentrics are preferably rotating in-phase with each other to minimize vibration. Preferably, shafts (113, 131 and 133), which connect the eccentrics to the drive pulleys rotated by belt (127), have single rotational axes.

In yet another embodiment, the eccentrics rotate and the storage assembly orbits but preferably does not rotate. The rotational position of the eccentrics about their shaft axis corresponds to the orbital position of the storage assembly about its central axis. The top eccentric (115) is preferably positioned to be about 180° out-of-phase with the rotating counter-weight (105). Counter-weight (105), which is provided to minimize the undesirable turbulence or the tendency to "walk" as best shown in FIG. 10(*c*), has an adjustable component 106 which can be moved toward or away from rotating shaft (113) to increase or decrease the angular momentum of the counter-weight. In one non-limiting example, the mass of the assay consumable storage assembly (103) is about 5,000 grams and the mass of the counterweight (105) is about 412 grams.

The system spring constant (k) of the assay consumable storage assembly (103) is preferably substantially high, so that the resonant frequency $$f = \frac{1}{2\pi}\sqrt{\frac{k}{m}},$$

where k is the system's spring constant and m is the system's mass, is substantially high. Preferably, the assay assembly (103)'s resonant or natural frequency is above the rotating frequency of the orbital shaker assembly (101). Preferably, the assay consumable storage assembly (103) contains no spring or damper.

Detailed views of a shelving subassembly (104) are shown in FIGS. 11(*a*)-(*c*). The shelving assembly includes a housing (201) having a top (202), a back (203), left and right housing walls, which can be double walls, (204 and 205, respectively), and a plurality of sets of vertically aligned storage units. In FIGS. 11(*a*)-(*b*) two sets of vertically aligned storage units are shown (206 and 207, respectively). Storage units within a set are aligned or stacked, (e.g., 208-209) and each storage unit includes an introduction aperture (210) and a door configured to seal the aperture (211).

The shelving subassembly comprises an array of sets of vertically aligned storage units. The array can be rectilinear, circular, or polygonal. In one embodiment, the array is an M×N rectilinear array of sets of vertically aligned storage units, wherein M and N are integers. One embodiment of a rectilinear array is shown in FIGS. 11(*a*)-(*b*) which includes two sets of storage units (206 and 207, respectively) adjacent to one another in the subassembly forming a 2×1 array. Alternative configurations of a rectilinear array are shown in FIGS. 11(*d*)-(*f*), which depict a 2×2 array (2(*d*)), 3×3 array (2(*e*)), and a 4×4 array (2(*f*)). In addition, the array can be polygonal or circular, as shown in FIGS. 11(*g*)-(*i*). If the array is polygonal, it is a regular polygon, e.g., a triangle, pentagon, hexagon, heptagon, octagon, nonagon, decagon, or a dodecagon, as shown in FIGS. 11(*g*) and 11(*h*), where X is an integer from 1-7. Alternatively, the array is circular, as shown in FIG. 11(*i*). In the embodiments shown in FIGS. 11(*g*)-(*i*), the array comprises 360°/P sets of storage units, wherein P is an integer and the sets of storage units are positioned within the shelving subassembly about a central axis (212-214, respectively).

Each shelving subassembly can include up to one hundred individual storage units, preferably up to forty individual storage units, and more preferably, up to twenty-four individual storage units. The skilled artisan will readily appreciate that numerous arrangements of storage unit sets in a shelving subassembly can be configured, varying in the number of sets as well as the number of vertically aligned storage units in a given set or collection of sets, as long as the apparatus includes a sufficient counterweight positioned within the storage assembly at a height corresponding to the resultant center of mass of the storage assembly and the orbiting platform. In a specific embodiment, each adjacent set of storage units sharing an adjoining wall (215; e.g., 206 and 207) comprise the same number of storage units.

Figure 12A:
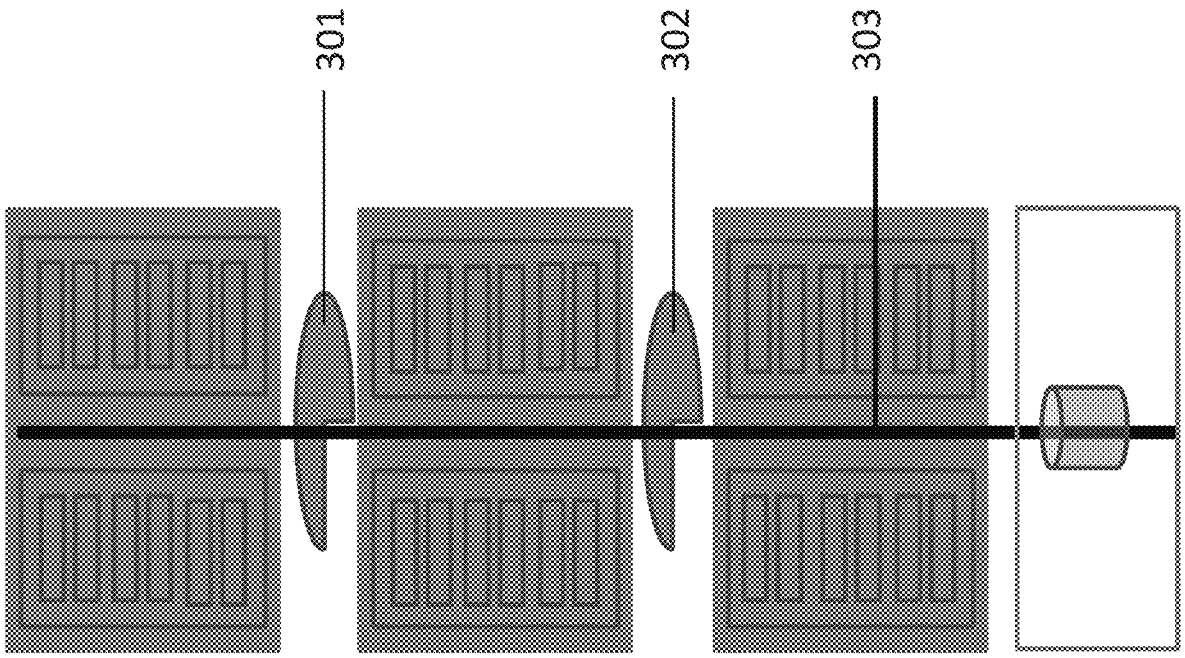
FIGS. 12(*a*)-(*b*) show two alternative configurations of sets of vertically aligned storage units within the storage assembly and counterbalance placements within the storage assembly relative to the storage unit sets.
Figure 12B:
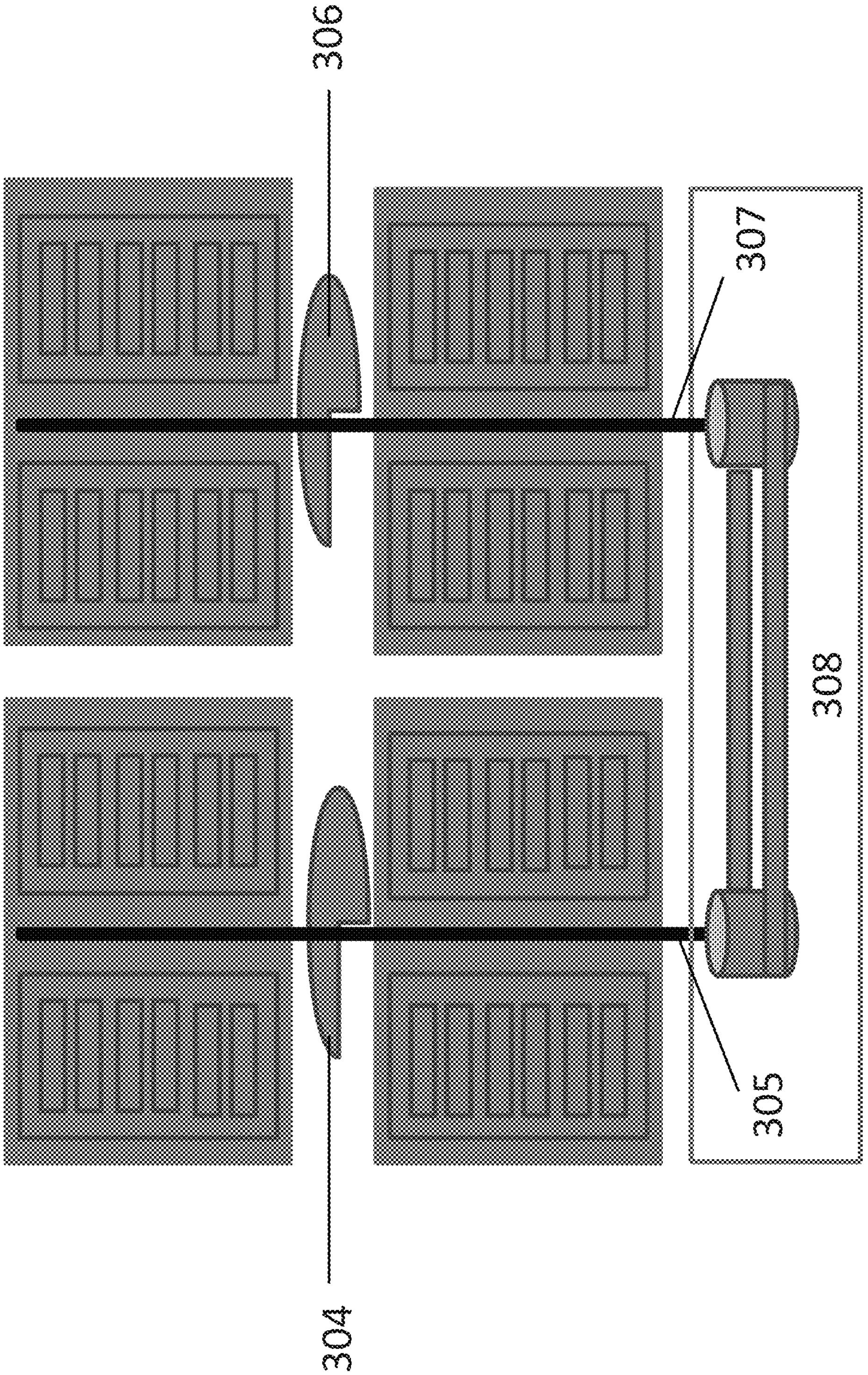
Figure 13A:
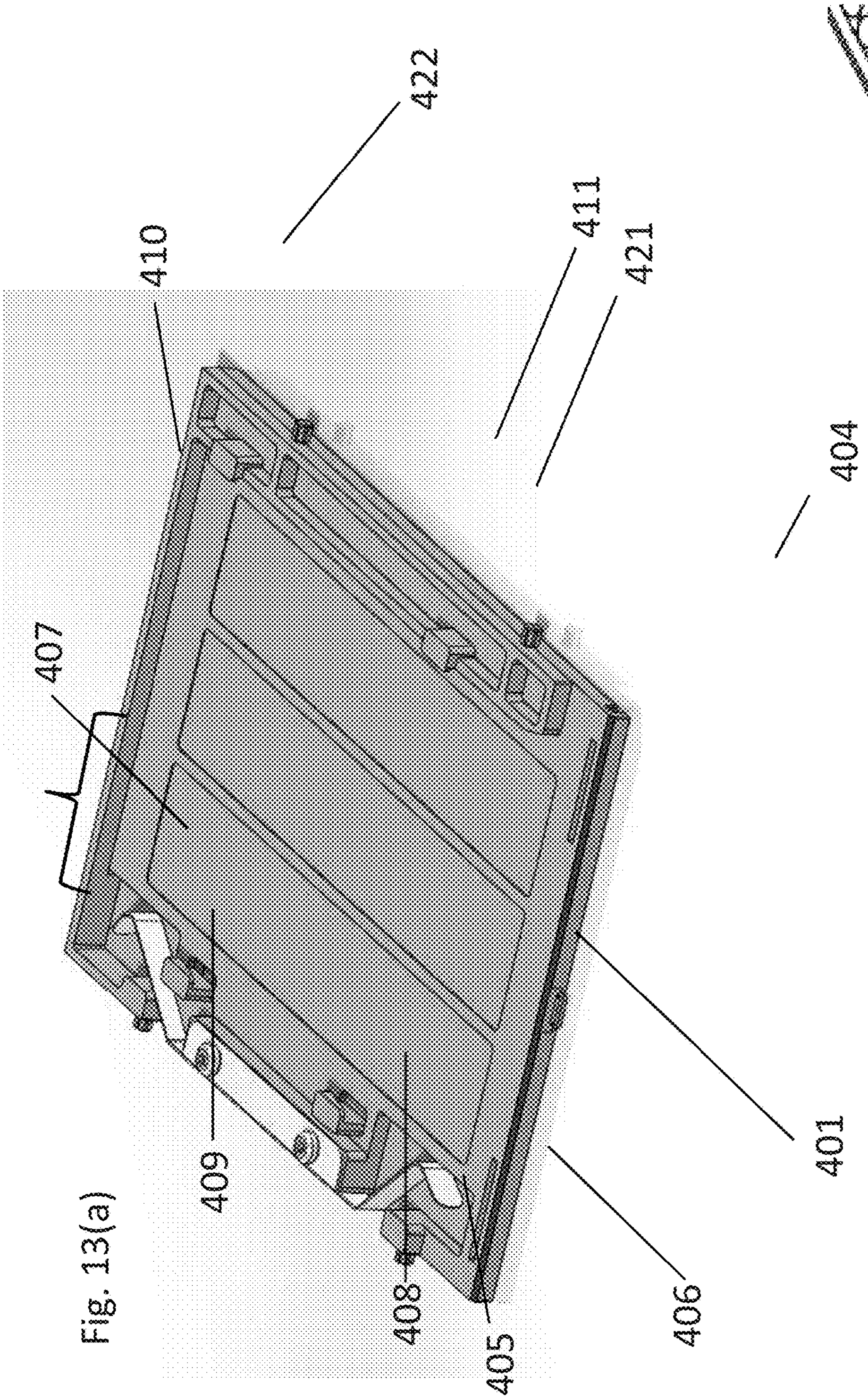
FIGS. 13(*a*)-(*d*) show one embodiment of a latching mechanism used in the storage units of the apparatus, where FIG. 13(*b*) is a partial view of a microtitre plate.
Figure 13B:
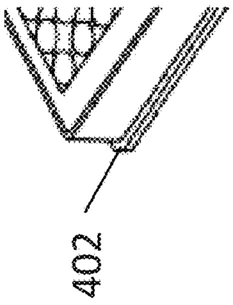
Figure 13C:
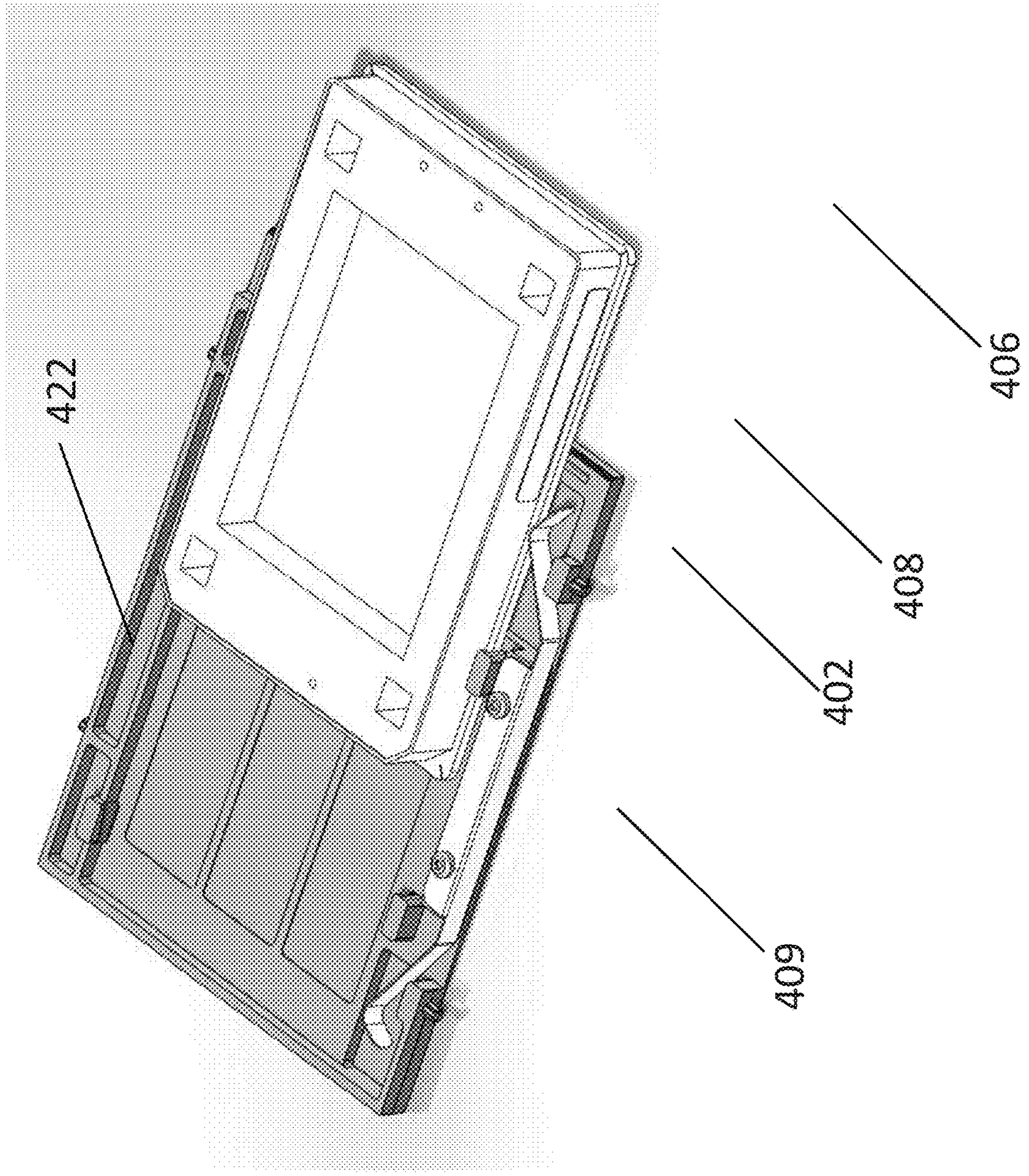
Figure 13D:
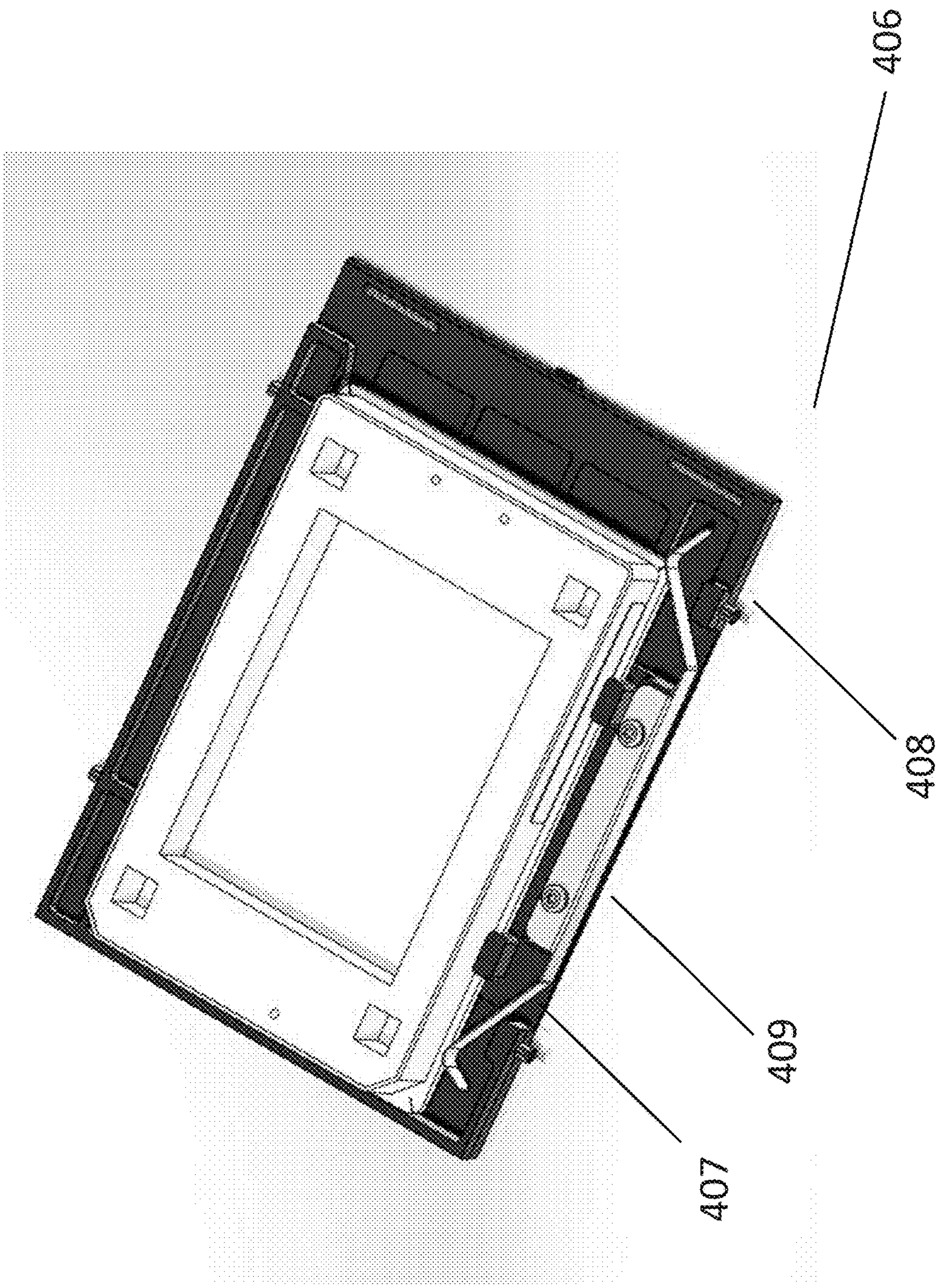

As shown in FIGS. 12(*a*)-(*b*), the apparatus can include two or more counterweights, where the multiple counterweights are distributed evenly so that the resulting center of mass of the multiple counterweights coincides with the resultant center of mass of the orbiting components. As described above, a single counterweight would be positioned to coincide with the center of mass of the orbiting components. In the embodiment shown in FIG. 12(*a*), the two or more counterweights (301 and 302, respectively) are in operative communication with one rotating axle (303). Preferably, counterweights (301, 302) are located symmetrically above and below a centroid plane of the system shown in FIG. 12(*b*). Alternatively, as shown in FIG. 12(*b*), a first counterweight (304) is in operative communication with a corresponding first rotating axle (305) and a second counterweight (306) is in operative communication with a corresponding second rotating axle (307), wherein each axle is driven by a timing belt (308) such that each rotating axle is driven in unison by the orbital shaker assembly. Preferably, counterweights (304, 306) are located at or near a centroid plane of the orbiting system shown in FIG. 12(*b*).

Any suitable orbital shaking mechanism can be used in the apparatus. As described in U.S. Pat. No. 5,558,437, the disclosure of which is incorporated herein by reference, conventional shaking mechanisms can drive the platform in an orbital translation and include one or more vertical shafts driven by a motor with an offset or crank on the upper end of an uppermost shaft such that the axis of the upper shaft moves in a circle with a radius determined by the offset in the shaft, i.e., by the crank throw. The upper shaft or shafts are connected to the underside of the platform via a bearing to disconnect the rotational movement between the upper shaft or shafts and the platform. On multi-shaft mechanisms, rotation of the platform is generally prevented by a four-bar-link arrangement of the shafts. On single shaft mechanisms, the rotation of the platform is generally prevented by connecting an additional linkage or a compliant linkage between the platform and base.

As described above, each storage unit is sized to accommodate an assay consumable, e.g., a microtitre plate, and includes a latching mechanism to secure the consumable within the storage unit. An exemplary plate latching mechanism is shown in FIGS. 13(*a*)-(*d*) which is configured to receive and engage an exemplary plate placed on the storage unit platform (401) (or a consumable having the same footprint and external physical geometry as a multi-well/microtitre plate configured for use in an apparatus as described herein). The plate has at least a first, second, third, and fourth sides, wherein the first and third sides are substantially parallel to each other and the second and fourth sides are substantially parallel to each other. The outside edges of the plate follow a standard design convention for multi-well/microtitre plates and include a skirt (402) that surrounds and is at a height lower than the walls of the plate (an enlarged view is shown in FIG. 13(*b*)). The plate latching mechanism is designed to push the outside edge of the skirt on two orthogonal sides of the plate against two corresponding physical stops in the plate platform, to apply a downward physical force in defined locations on the top of the plate skirt to reproducibly and fixedly hold the plate.

In the embodiment shown in FIG. 13(*a*), the plate latching mechanism (403) is perpendicular to the platform edge aligned with the plate introduction aperture of the storage unit (404). The plate latching mechanism comprises a latching member (405) biased to the clamping position and consisting of two pedals (406 and 407, respectively). Two cleats (408 and 409, respectively) located on the same side as pedals (406, 407) and two cleats (421, 422) located on the opposite side configured to vertically constrain the plate skirt. Referring to FIG. 13(*c*), the first pedal (406) is adapted to push the first side of the multi-well plate toward the first cleat (408) which engages with the plate skirt (402). The first cleat (408) engages with the plate skirt and provides a hard mechanical limit to the vertical movement of the plate. As the plate is pushed toward the inside of the platform, the second cleat (409) engages with the plate skirt and further restrains vertical movement of the skirt of the plate. As shown in FIG. 13(*d*), when the plate is fully inserted on the platform and the latching mechanism is completely engaged, first and second cleats (408, 409) along with opposite third and fourth cleats (421, 422) engage the plate skirt and limit the plate's vertical movement. Pedal (407) provides a lateral bias to the plate and pedal (406) provides both a lateral and rearward bias to the plate. In the embodiment shown in FIG. 13(*d*), the plate is pushed against the rear end of the plate platform (410), opposite the plate introduction aperture, as well as the side of the platform opposite the latching mechanism (411).

Figure 14B:
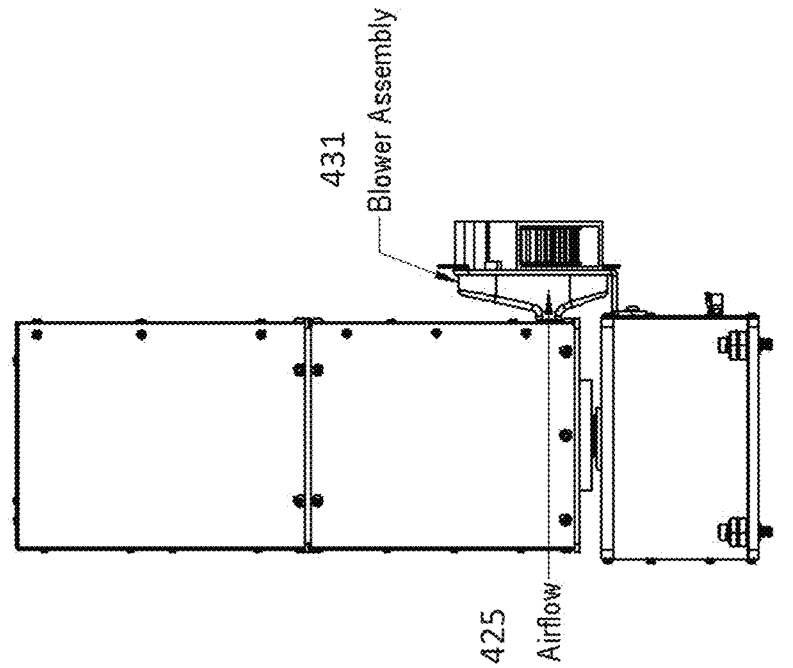
FIGS. 14(*a*)-(*b*) show an embodiment of the shaker apparatus with an internal air flow path.
Figure 14A:
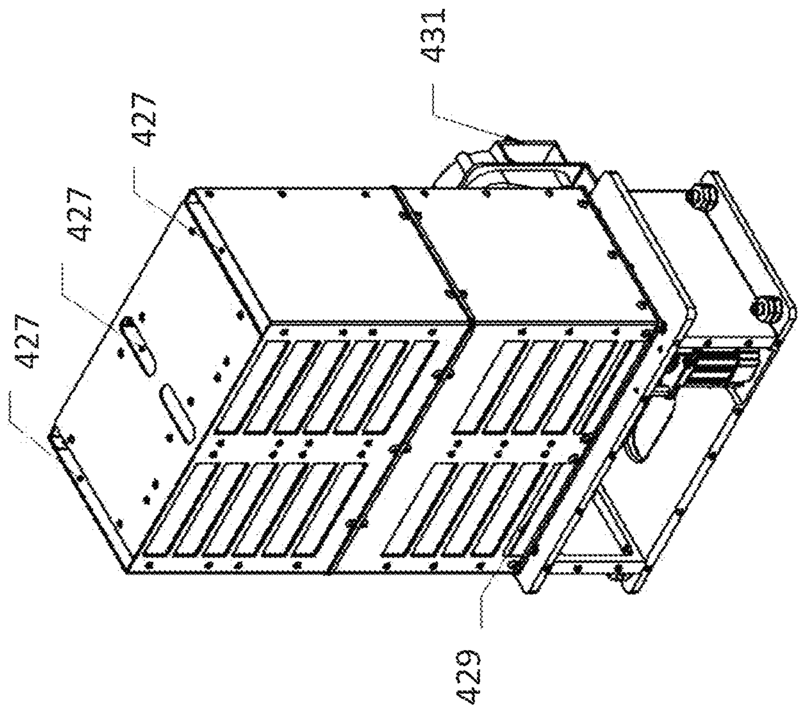

According to another aspect of the present invention, an optional air flow path (425) is provided internal to assay consumable storage assembly (103), as best shown in FIGS. 14(*a*) and 14(*b*). This air flow path (425) comprises a number of vertical air shafts (427) interconnecting with a number of horizontal air shafts (429) between horizontal orbiting platform (102) and the lower shelving subassembly (104) to allow cooling air to flow through or to circulate through assay consumable storage assembly (103), and preferably between vertically aligned storage units (106-109). An air exhaust or blower assembly (431) is provided to pull air through this gap. Alternatively, the air exhaust or blower assembly (431) may push air into air flow path (425). Another optional air shaft may be provided in the space between the upper shelving subassembly 104 and the lower shelving subassembly 104.

Example 1

System 10 is designed for ultra-high throughput testing of clinical samples with ECL detection technologies, such as those from Meso Scale Diagnostics ("Meso Scale") of Rockville, Maryland. To achieve high throughput, system 10 uses multiplexed testing in a 96-well plate format and can process batches of up to 20 plates. It has a central robot arm 26 that transfers plates between components that perform different assay steps: a 96 channel pipettor 32, barcode reader, plate washer 30, plate shaker 28 and a plate ECL reader 36 from Meso Scale. System 10 is a free-standing fully automated system. System 10 is functional and beta units are in use at Meso Scale.

Key features of the system 10's platform include, but not limited to:

1. Batch processing of up to 20 assay plates (1600 samples per batch assuming 80 samples per plate (singlicate)+16 wells used for calibrators or controls)
2. Throughputs as high as 12,800 samples per day (8 batches of 20 plates per day)
3. All pipetting and washing steps are performed using 96-channel components capable of processing all the wells in a plate simultaneously
4. Assay processing is carried out in a temperature controlled enclosure and all steps are precisely timed to provide highly reproducible and precise results
5. A custom designed shaker (described in commonly owned provisional application Ser. No. 62/143,557, incorporated herein in its entirety) with a 20 plate capacity provides rapid antibody binding kinetics; each plate is incubated in a separate enclosed chamber within the shaker to prevent evaporation
6. Ability to carry out samples dilutions
7. Simple scheduling approach does not require interleaving of assay operations.

System 10 uses individual off-the-shelf and custom built components that function together as one fully automated system. The off-the-shelf components include a MESO QuickPlex® SQ 120 Reader (available from Meso Scale), a BioTek® 96-channel plate washer, a Precise Automation® plate handling robot, a barcode reader and an Apricot Designs™ 96-channel pipetting head. The custom built components of the platform include a plate hotel/shelves, a 20-plate shaking incubator, two pipette tip washing manifolds, a four-plate pipetting deck, and a pipettor gantry to support the pipetting head. The deck and all components are located within an enclosure with heating/cooling units that maintain the enclosure at a set temperature (FIGS. 2 and 3).

The platform attains ultra-high throughput by processing entire 96-well plates at once using 96-channel components. This approach allows the processing operations to be divided into a series of processing cycles separated by incubation periods, where the time associated with any specific processing cycle is a discrete amount of time, for example, less than 3 minutes. It is, therefore, possible to schedule each cycle on each plate to be carried out in 3 minute intervals, simplifying the scheduling of operations while maintaining tight control over the timing of each cycle. By separating each assay cycle with binding reaction incubation times of one hour, batches of plates, e.g., 20, can be run while maintaining the 3 minute intervals between plates over multiple assay cycles. The system can be expanded for even higher throughput.

By way of a non-limiting example, in the case of a biodosimetry test (see Example 2), system 10 runs a single incubation assay with the following automated assay processing steps, divided into cycles:

1. Sample addition cycle:
   - a. Robot removes source plate (with samples), reagent reservoir (with detection antibody solution) and assay plate (MSD® Multi-Array plate with capture antibody array from Meso Scale) from plate hotel/shelves and places on the deck
   - b. Robot lifts lid from source plate to allow pipettor access
   - c. Pipettor transfers sample and detection antibody to wells of assay plate
   - d. Robot transfers assay plate to shaker for one hour incubation
   - e. Pipette tips are washed using tip washing manifolds
2. Plate read cycle (scheduled one hour after step 1):
   - a. Robot removes assay plate from shaker and places on washer
   - b. Plate washer washes wells three times with wash buffer to remove sample
   - c. Robot moves assay plate and reagent reservoir with read buffer to deck
   - d. Pipettor transfers read buffer to wells of assay plate
   - e. Robot transfers plate to MSD SQ120 plate reader for analysis By maintaining the 3 minute interval between plates, it is possible to process 20 plates in a batch with a time-to-first result of 1 hour and a time-to-final result of 2 hours, while maintaining strict control of the timing of each cycle. Optionally, the binding of sample and detection antibody may be separated into two separate cycles with separate 1 hour incubations to achieve optimal assay performance. In this case, the time-to-first result would be 2 hours and the time-to-final result would be 3 hours for a 20 plate batch.

To prepare the system and reagents to run the biodosimetry test on a batch of 20 plates, the operator would follow the process described below:

- Lyophilized detection antibody is rehydrated and transferred to a reagent reservoir
- Read buffer, supplied as a liquid bulk reagent, is added to a second reagent reservoir
- Lyophilized calibrators and controls (supplied with kit in tubes with the kit) are rehydrated
- Samples, controls and calibrators are transferred from tubes into 96-well source plates
- Columns 1 and 2 on the plates are reserved for a 7-point calibration curve run in duplicate and 2 controls; columns 3 to 12 are used for 80 samples)
- This step can be performed manually or, for higher throughput, with automated sample transfer workstations that are found in most clinical laboratories
- The user logs into the system using his or her login credentials
- The user selects the assay type (Biodosimetry Test in this case); this defines the assay protocol setup including the dispense volumes, incubation times, etc.
- Following graphical diagrams provided by the software, the user adds the MSD assay plates, source plates and reagent reservoirs to the plate rack
- The system runs a setup routine that takes inventory of all source plates (barcodes are read) and reagent reservoirs to confirm the location of all components; the system also confirms with the user that the bulk reagents have been replaced
- The system executes the automated Biodosimetry assay protocol (described above)
- Used assay plates and reservoirs are removed from the plate hotel/shelves
- Results are calculated by the software and displayed on the touchscreen GUI System 10 can process 20 plates within 2 hours. For highest throughput, the next set of 20 sample source plates (containing sample, calibrators and controls) can be prepared while the current set of 20 plates is running. The source plates can be prepared manually, however commercial off-the-shelf systems for sample reformatting can be used to more efficiently complete this task and maintain the same throughput as system 10. Automated systems found in most large clinical laboratories can centrifuge blood tubes, de-cap tubes, and pipet plasma samples into a pre-defined layout into system 10's sample source plates. These systems can also be programmed to transfer calibrators and controls to the sample source plates, or the user can perform this task manually once the samples have been processed and added to the source plates. The software for system would have the capability of communicating with these automated systems to upload the locations of each sample (identified by a unique barcode ID) within each source plate (also identifiable by a unique barcode ID).

Example 2: Biodosimetry Assay

Detailed descriptions of biodosimetry assays and algorithms that can be carried out using an instrument and/or methods in accordance with the invention are described in U.S. application Ser. No. 14/348,275, (U.S. Publication No. 2014/0315742) which is incorporated by reference herein in its entirety. Included in the application is the use of a panel of six radiation biomarkers in plasma or blood (Flt-3L, CD20, CD177, TPO, LBP, salivary amylase) to estimate the dose of exposure of an individual that may have been exposed to radiation. This specific panel is described for illustrative purposes. The invention encompasses use of the instrumentation and methods described herein to conduct assays for any one of these biomarkers whether alone or in combination with other analytes, or any combination of two, three, four, or five of these biomarkers, with or without other analytes contained in the same assay panel. Specifications for such a test on System 10 are outlined below:

TABLE

Specifications for the Biodosimetry Test Conducted on System 10.

| | Specification | Details |
|---|---|---|
| **General Specifications** | | |
| Number of biomarkers | 6 biomarkers<br>2 internal controls | System 10 supports 25-plex measurements<br>Biodosimetry test has 6 biomarkers (Flt-3L, CD20, CD177, TPO, LBP, salivary amylase) and 2 internal procedural controls |
| Sample type | Plasma | K2EDTA plasma from a venous draw |
| Sample volume | 50 μl | |
| Time to result (20 plate batch; 1,600 samples) | 1 hr (1st result)<br>2 hr (final result) | Assuming single 1 hour incubation |
| Throughput (samples/day) | 12,800 samples | Assuming 8 batches of 20 plates per day, 80 samples per plate run in singlicate, and 16 wells used for calibrators or controls |
| Result reporting | Visual and electronic | Visual: results on touch screen interface<br>Electronic: results stored on system and available through network interface |
| Patient tracking | Patient ID linked to results | Patient ID will be electronically linked to test results in records; barcodes can be used for patient IDs |
| Internal procedural controls | Yes | Negative and positive internal procedural controls based on artificial antigens |
| External QC controls | Yes | Positive control (mimics moderate dose)<br>Negative control (mimics no exposure) |
| Calibration of biomarker assays | Yes | Each plate is independently calibrated using a set of calibrators containing all 6 biomarkers |
| **Performance of Biodosimetry Test** | | |
| Measurable dose range | 0.5-10 Gy | Assesses dose over wide dose range |
| Time window for testing (time of samplecollection) | 24 hrs—7 days post-exposure | Dose assessment up to 20 days post-exposure may be possible |
| Dose accuracy: | | |
| Doses <2 Gy | ±0.5 Gy | Quantitative assessment of dose |
| Doses ≥2 Gy | ±25% | |
| Clinical sensitivity | 99% | For patients receiving doses ≥2 Gy |
| Clinical specificity | 97% | For unexposed individuals |
| **Performance of Individual Biomarker Assays** | | |
| Assay precision | ±10% (15%) | Intra-run (inter-run) coefficients of variation |
| Assay linearity | ±20% | Linearity of biomarker quantitation in relevant concentration range |
| **Instrument Properties** | | |
| Temperature—ambient | 20° C. to 26° C. | Allowable environmental temperature range |
| Temperature—assay | 23° C. ± 1° C. | Temperature variation inside System 10 |
| Size | Fits on pallet | 5' × 3' × 5' (W × D × H) |
| Power | Standard 120 or 208/240 VAC | 208-240 VAC |
| Ramp-up time | ≤1 hour | Time to reach internal temperature set point |
| Uptime/maintenance | 23 hrs/day uptime<br>≤1 hr maintenance | Maintenance includes replenishing buffers, emptying waste, and performing cleaning cycles on the plate washer |
| Ease of use/Test category | CLIA moderately complex | Fully automated laboratory instrument with barcoded sample tracking |

TABLE-continued

Specifications for the Biodosimetry Test Conducted on System 10.

| | Specification | Details |
|---|---|---|
| **Test Consumables** | | |
| Test kit components | Assay Materials required to run 20 plates | Each test kit contains:<br>20 assay plates (96-well MULTI-ARRAY)<br>Detection reagent (lyophilized)<br>Calibrators (lyophilized)<br>Assay diluent (dry)<br>External controls (lyophilized)<br>Package insert |
| Kit shelf life | ≥3 years | Shelf life is for consumables stored at 4° C.; all biological reagents will be in a dry format for maximum reagent stability and long shelf life |
| Bulk Consumables and Fluids | Additional consumables and fluids needed to run system | Sample source plates<br>Pipette tips<br>Reagent reservoirs<br>Wash buffer<br>Read buffer<br>DI water<br>Plate lids |
| Bulk fluid shelf life | ≥3 years | Room temperature storage |

Assay Formats that can be Run on System 10

System 10 can be configured to run any number of assay formats by modification of the processing cycles (as described above) used to process assay plates. Several illustrative examples are provided below for different immunoassay formats, although the basic approaches are clearly applicable to other assay types including binding assays using non-antibody based binding reagents (e.g., nucleic acid hybridization assays). System 10 is specifically designed for carrying out assays using ECL detection and Meso Scale (MSD) MULTI-ARRAY® assay plates, but the approaches are applicable to techniques using other multi-well plate consumables and detection technologies.

The different assay formats are described through a table that lists the processing cycles used by System 10 to complete the assay process. Each cycle may comprise one or more of the following assay steps: (i) using the robotic arm to select a target plate from the hotel or shaker and moving the plate to the washer for a plate wash, (ii) using the robotic arm to move the target plate to the pipetting deck for pipetting operations, (iii) and (iv) selection of up to two source/reagent plates including moving the plates from the hotel to the pipetting deck and using the pipettor to transfer solutions to the target plate, (v) pipette tip wash (after each plate or only after the last plate undergoing a specified cycle), (vi) transfer of the target plate to an incubation location where incubation can be carried out with shaking (i.e., in the shaker) or without shaking (in the plate hotel) and (vii) transfer to the plate reader for carrying out the assay measurement. The table lists which steps are carried out in each cycle and identifies the target and source/reagent plates by content, where "capture", "detection" and "sample" refer to source/reagent plates that contain capture reagents, detection reagents, or samples, respectively.

Two-Step Sandwich Immunoassay. In the two-step sandwich immunoassay, the wells of a MSD assay plate (with one capture antibody or an array of capture antibodies immobilized on the bottom of each well) are incubated first with sample diluted in an assay diluent and then with labeled detection antibodies prior to measurement of the labeled sandwich complexes that form. The protocol as shown includes a blocking cycle as the first cycle; optionally, this cycle may be omitted. One simple variation of this protocol includes an additional cycle (3a) between cycles 3 and 4.

This protocol is used when the detection reagent in cycle 3 does not comprise a label of the type detected in the reader. Cycle 3a is like cycle 3 except that Source Plate 1 contains a labeled secondary reagent that binds the detection reagent, with a label appropriate for the reader. The use of a labeled secondary detection reagent is well known in the art. Specific examples include the use of labeled anti-species antibodies to detect antibody detection reagents, or the use of labeled streptavidin to detect biotin containing detection reagents.

| Cycle | Description | Wash | Target Plate | Source Plate 1 | Source Plate 2 | Tip Wash | Incubation | Read |
|---|---|---|---|---|---|---|---|---|
| 1 | Block Plate | No | MSD Assay | Blocker | None | After last plate | Static or Shaking | No |
| 2 | Add Sample | Yes | MSD Assay | Sample | Diluent | After each plate | Shaking | No |
| 3 | Add Detection | Yes | MSD Assay | Detection | None | After last plate | Shaking | No |
| 4 | Read | Yes | MSD Assay | Read buffer | None | None | No | Yes |

Sandwich Assay Including Antibody Immobilization Step. This protocol is similar to the sandwich assay described above except that instead of using an assay plate pre-coated with a capture antibody, the assay plate is either uncoated or coated with a generic capture reagent such as streptavidin. The protocol, therefore, includes an additional cycle during which the capture antibody is adsorbed onto the uncoated plate or capture by binding to the capture reagent (for example, through the binding of a biotin-labeled capture antibody to immobilized streptavidin in the well). As in the previous table, the blocking cycle may be omitted. The protocol as described in the table can be used to immobilize a single capture reagent per well, or can be used for the solution phase assembly of an array of capture reagents as described in US Published Patent Application No. 20140256588. For example, the wells in the assay plate may each have an immobilized array of different targeting reagents (e.g., oligonucleotides), and the capture reagent (i.e., the contents of Source Plate 1 in Cycle 1) may be a mixture of different capture reagents linked to different targeting reagent complements (e.g., oligonucleotides complementary to the targeting agents), such that when this mixture is incubated in a well, the targeting reagents and their complements bind and the different capture reagents immobilize on different elements of the targeting reagent array to form a capture reagent array.

| Cycle | Description | Wash | Target Plate | Source Plate 1 | Source Plate 2 | Tip Wash | Incubation | Read |
|---|---|---|---|---|---|---|---|---|
| 1 | Coat Capture | No | MSD Assay | Capture | None | After last plate | Shaking | No |
| 2 | Block Plate | Yes | MSD Assay | Blocker | None | After last plate | Static or Shaking | No |
| 3 | Add Sample | Yes | MSD Assay | Sample | Assay Diluent | After each plate | Shaking | No |

-continued

| Cycle | Description | Wash | Target Plate | Source Plate 1 | Source Plate 2 | Tip Wash | Incubation | Read |
|---|---|---|---|---|---|---|---|---|
| 4 | Add Detection | Yes | MSD Assay | Detection | None | After last plate | Shaking | No |
| 5 | Read | Yes | MSD Assay | Read buffer | None | None | No | Yes |

Bridging Immunogenicity/Serology Assay. In this protocol, antibodies against a specific antigen or drug are identified by their ability to simultaneously bind two copies of the antigen or drug to form a sandwich complex. In the embodiment described in the table a mixture ("mastermix") of antigen linked to biotin (or some other binding reagent) and antigen linked to a label detectable in the System 10 plate reader (such as an ECL label) is aliquoted into a plate (the Mastermix plate). Sample and acid are transferred into a plate (the Treatment plate), so as to dissociate any antibody complexes that may be present in the sample. The acid-treated sample and a neutralization buffer are then combined with mastermix in the mastermix plate and incubated to allow the formation of sandwich complexes comprising biotin-antigen, antibody-of-interest, and labeled-antigen. The resulting solutions are then transferred to an assay plate having wells comprising immobilized streptavidin (or an appropriate binding partner for the binding reagent linked to the antigen) and incubated to capture the sandwich complex to the immobilized streptavidin where it can be measured in the plate reader. In some cases, it may be desired to run this protocol without acid dissociation, in which case the acid in Source Plate 1 in Cycle 3 may be replaced with a non-acidic dilution buffer and, optionally, the neutralization buffer may be omitted or replaced with an assay diluent. Alternatively, Cycle 3 may be omitted completely and sample may be added directly to the Mastermix plate in Cycle 4 (i.e., Source Plate 2 is a sample plate). Note that since the incubations after Cycles 1 and 2 occur in the plate hotel, these incubations may continue in parallel with the incubations of later cycles until the resulting plates are required in Cycles 4 and 5, respectively.

| Cycle | Description | Wash | Target Plate | Source Plate 1 | Source Plate 2 | Tip Wash | Incubation | Read |
|---|---|---|---|---|---|---|---|---|
| 1 | Aliquot Mastermix | No | Mastermix | Mastermix Reservoir | None | After last plate | Static | No |
| 2 | Block Plate | No | MSD Assay | Blocker | None | After last plate | Static | No |
| 3 | Acid Dissociation | No | Treatment Plate | Acid | Sample | After each plate | Shaking | No |
| 4 | Sample + Mastermix | No | Mastermix | Neutralization Buffer | Treatment Plate | After each plate | Shaking | No |
| 5 | Load Assay Plate | Yes | MSD Assay | Mastermix | None | After each plate | Shaking | No |
| 6 | Read | Yes | MSD Assay | Read buffer | None | None | No | Yes |

Amplified Immunoassay. System 10 may be used to carry out binding assays that employ an amplification step to increase sensitivity. In the example of a Two-Step Immunoassay described above, the process may include an additional amplification cycle (3a) between cycles 3 and 4 to prepare for or carryout the amplification procedure. In the case that the detection reagent includes an enzyme label, the cycle 3a could include adding an enzyme substrate (in Source Plate 1) to the assay plate (the Target Plate) where conversion of the substrate by the enzyme leads is detectable by the reader. Alternatively, cycle 3a could be omitted and the substrate could be added from Source Plate 1 or 2 in cycle 4, just prior to transfer of the assay plate to the reader. In the case that the detection reagent includes a nucleic acid label, cycle 3a could include adding the reagents for amplifying the label from Source Plates 1 and/or 2 (e.g., by PCR or isothermal nucleic acid amplification), the amplification being carried out in the subsequent incubation period. The table below describes the automated assay process for carrying out an amplified binding assay as described US Published Patent Application No. 20140272939 in the context of an immunoassay using antibodies as analyte binding reagents, although the process could clearly be applied to assays using other types of binding reagents. Each well of the MSD Assay Plate has an immobilized capture antibody that is, optionally, co-immobilized with an anchoring reagent comprising an anchoring oligonucleotide sequence. The procedure includes an optional blocking cycle (Cycle 1), followed by cycles for adding sample to bind analyte to the capture antibody (Cycle 2) and for adding detection reagent to bind to the captured analyte (Cycle 3). In this embodiment, the detection reagent is a mixture of a first detection antibody linked to a first nucleic acid probe and a second detection antibody linked to a second nucleic acid probe, both of which bind to captured analyte to form a complex on the well surface comprising the capture antibody, the analyte and both detection antibodies. In the ligation cycle (Cycle 3), a ligation mixture is added to each well comprising a ligase and one or more connector nucleic acid sequences that are linear sequences that comprise regions complementary to the first and second probes, so that when incubated in the presence of one of the complexes of capture antibody, analyte and first and second detection antibodies, the connector sequence(s) are ligated to form a circular nucleic acid sequence hybridized to the first and second probes in the complex. If the optional anchoring oligonucleotide is included, the connector sequence(s) include an anchoring region that matches a region of the anchor sequence (i.e., they both hybridize to the same complementary sequence). In the amplification cycle (Cycle 4), an amplification mixture is added to each well comprising a DNA polymerase and a labeled detection probe (comprising a detection sequence that matches a detection region in the connector sequence(s)). When the amplification mixture is incubated in the presence of the circular nucleic acid bound to the first and second probes, the first probe is extended by rolling circle amplification and the labeled detection probes bind to the extended product. The extended product also binds to the anchoring reagent, if present. In the read cycle, read buffer is added to the wells and labeled probe is detected in the reader to measure the presence of the analyte.

| Cycle | Description | Wash | Target Plate | Source Plate 1 | Source Plate 2 | Tip Wash | Incubation | Read |
|---|---|---|---|---|---|---|---|---|
| 1 | Block Plate | No | MSD Assay | Blocker | None | After last plate | Static or Shaking | No |
| 2 | Add Sample | Yes | MSD Assay | Sample | Diluent | After each plate | Shaking | No |
| 3 | Add Detection | Yes | MSD Assay | Detection Ab mixture | None | After each plate | Shaking | No |
| 4 | Ligation | Yes | MSD Assay | Ligation mixture | None | After last plate | Shaking | No |
| 5 | Amplification & Detection | Yes | MSD Assay | Amplification mixture | None | After last plate | Shaking | No |
| 6 | Read | Yes | MSD Assay | Read buffer | None | None | No | Yes |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A method of performing an assaying protocol for each plate of a number of assay plates, the method comprising:

performing one of a series of timed processing cycles on a first plate of the number of assay plates, wherein each of the series of timed processing cycles are of equal duration and include at least one step selected from the group consisting of:

(a) pulling, from a shelf, the first plate from the number of assay plates;

(b) washing the first plate at a plate washer;

(c) pulling a blocking reagent reservoir from the shelf, and adding blocking reagents to the first plate from the blocking reagent reservoir using a pipettor;

(d) adding samples to the first plate using the pipettor;

(e) pulling a detection reagent reservoir from the shelf, and adding a detection reagent to the first plate from the detection reagent reservoir using the pipettor; and (f) pulling a read buffer reservoir from the shelf, and adding a read buffer to the first plate from the read buffer reservoir using the pipettor;

processing the first plate via the one of the series of timed processing cycles to completion before a next plate of the number of assay plates is processed;

placing the first plate from a deck into an orbital shaker assembly after the step of processing the first plate to completion, the orbital shaker assembly including an orbiting platform, and an assay consumable storage assembly positioned on the orbiting platform;

incubating the first plate in the orbital shaker assembly for an incubation period; and repeating each step of the assaying protocol for the next plate of the number of assay plates;

wherein the incubation period of each plate divided by a processing period for each plate equals the number of assay plates to be processed.

2. The method of claim 1, wherein the steps of adding the blocking reagents to the first plate using the pipettor, adding the samples to the first plate using the pipettor, adding the detection reagent to the first plate using the pipettor, or adding the read buffer to the first plate using the pipettor are performed on each plate in the number of assay plates on the deck.

3. The method of claim 1, further comprising a step of placing each subsequent plate of the number of assay plates in a reader after each subsequent plate is processed.

4. The method of claim 1, wherein the assaying protocol is performed by an electrochemiluminescence immunoassay system.

5. The method of claim 1, wherein the series of timed processing cycles are performed as individual automated operations.

6. The method of claim 5, wherein the series of timed processing cycles are performed as individual automated operations by a fully automated system.

* * * * *